United States Patent
Saito et al.

(10) Patent No.: US 7,728,969 B2
(45) Date of Patent: Jun. 1, 2010

(54) METHODS AND SYSTEMS FOR IDENTIFYING DEFECT TYPES ON A WAFER

(75) Inventors: Jason Saito, Milpitas, CA (US);
Wei-Ning Shen, Cupertino, CA (US)

(73) Assignee: KLA-Tencor Technologies Corp., Milpitas, CA (US)

( * ) Notice: Subject to any disclaimer, the term of this patent is extended or adjusted under 35 U.S.C. 154(b) by 45 days.

(21) Appl. No.: 11/949,473

(22) Filed: Dec. 3, 2007

(65) Prior Publication Data

US 2008/0129988 A1   Jun. 5, 2008

Related U.S. Application Data

(60) Provisional application No. 60/868,625, filed on Dec. 5, 2006.

(51) Int. Cl.
*G01N 21/00* (2006.01)

(52) U.S. Cl. .................. 356/237.5; 356/237.1

(58) Field of Classification Search ... 356/237.1–237.6, 356/239.1, 239.7–239.8, 364–369, 432, 73, 356/625, 394, 600–601, 630–632, 445–446, 356/429–431, 239.3, 337–343; 250/200–201.1, 250/559.19, 559.24, 559.22, 559.4–559.46, 250/559.27, 559.01, 559.11, 559.16
See application file for complete search history.

(56) References Cited

U.S. PATENT DOCUMENTS

| | | | |
|---|---|---|---|
| 6,201,601 B1 | 3/2001 | Vaez-Iravani et al. | |
| 6,271,916 B1 | 8/2001 | Marxer et al. | |
| 6,407,373 B1 | 6/2002 | Dotan | |
| 6,538,730 B2 | 3/2003 | Vaez-Iravani et al. | |
| 6,590,645 B1 | 7/2003 | Chen et al. | |
| 6,891,610 B2 | 5/2005 | Nikoonahad et al. | |
| 6,891,611 B1 | 5/2005 | Vaez-Iravani et al. | |
| 6,917,419 B2 | 7/2005 | Fielden et al. | |
| 6,922,236 B2 | 7/2005 | Vaez-Iravani et al. | |
| 6,956,644 B2 | 10/2005 | Biellak et al. | |
| 7,016,031 B2 | 3/2006 | Chen et al. | |

(Continued)

FOREIGN PATENT DOCUMENTS

WO   WO 99/67626   12/1999

OTHER PUBLICATIONS

International Search Report and Written Opinion for PCT/US07/86508 dated Apr. 24, 2008.

*Primary Examiner*—Gregory J Toatley, Jr.
*Assistant Examiner*—Tri T Ton
(74) *Attorney, Agent, or Firm*—Ann Marie Mewherter

(57) ABSTRACT

Various methods and systems for identifying defect types on a wafer are provided. One computer-implemented method for identifying defect types on a wafer includes acquiring output of an inspection system for defects detected on a wafer. The output is acquired by different combinations of illumination and collection channels of the inspection system. The method also includes identifying defect types of the defects based on the output acquired by a set of the different combinations. The set of the different combinations is selected based on the defect types to be identified on the wafer and a wafer type of the wafer such that a different set of the different combinations of the illumination and collection channels is used for identifying different defect types on different wafer types.

18 Claims, 14 Drawing Sheets

U.S. PATENT DOCUMENTS

| | | | |
|---|---|---|---|
| 7,038,772 B2 | 5/2006 | Chen et al. | |
| 7,106,425 B1 | 9/2006 | Bultman et al. | |
| 7,187,438 B2 | 3/2007 | Hamamatsu et al. | |
| 7,315,366 B2 | 1/2008 | Hamamatsu et al. | |

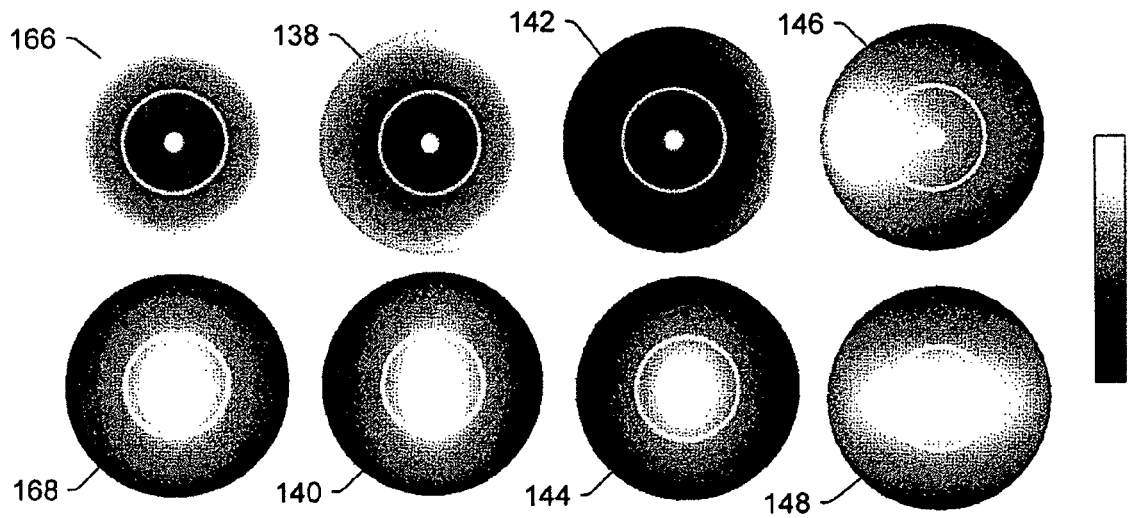
*Fig. 7*
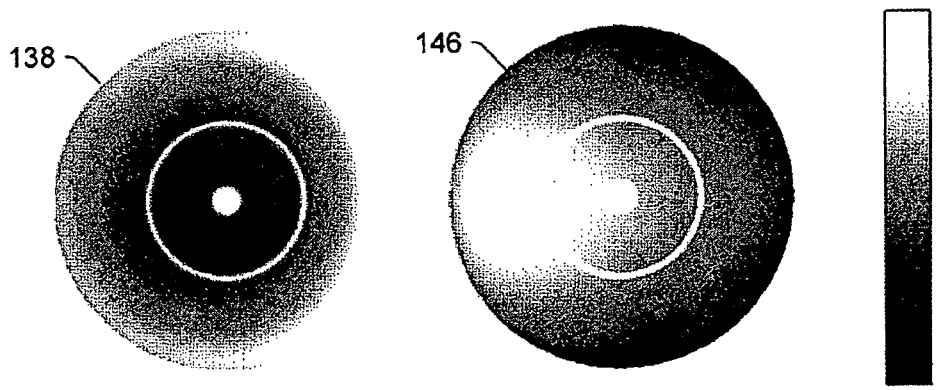
*Fig. 8*
| LPD-N COP Classification Accuracy and Purity ||||
|---|---|---|---|
| | SEM Review || |
| | COP | LPD/Scratch | Purity |
| RTDC  COP | 38 | 0 | 100% |
| RTDC  LPD/Scratch | 1 | 28 | 97% |
| Accuracy | 97% | 100% | |
*Fig. 9*

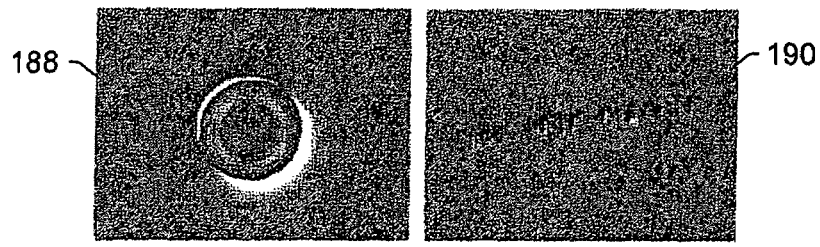
Fig. 12
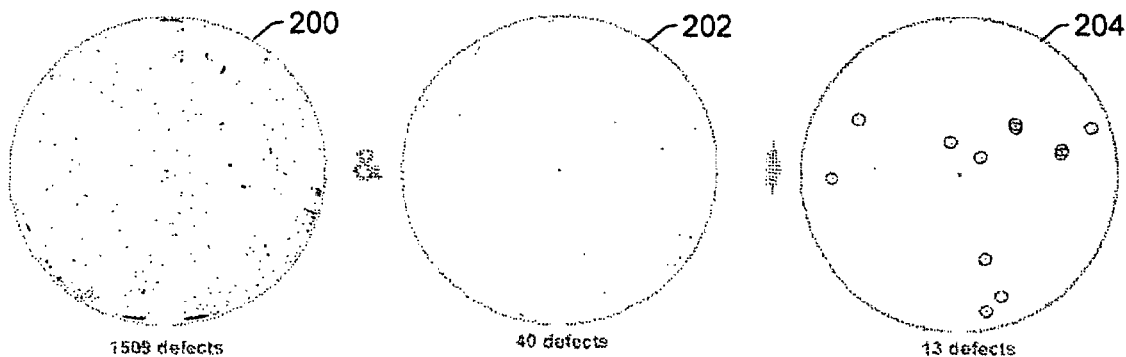
Fig. 13
| LLPD Classification Accuracy and Purity | | | |
|---|---|---|---|
| | SEM Review | | |
| | LLPD | LPD | Purity |
| RTDC LLPD | 12 | 1 | 92% |
| RTDC LPD | 0 | 1498 | 100% |
| Accuracy | 100% | 100% | |
Fig. 14

| Stacking Fault Classification Accuracy and Purity | | | | |
|---|---|---|---|---|
| | | SEM Review | | |
| | | SF | LPD/Residue | Purity |
| RTDC | SF | 11 | 0 | 100% |
| | LPD/Residue | 0 | 52 | 100% |
| | Accuracy | 100% | 100% | |

| Void Classification Accuracy and Purity | | | |
|---|---|---|---|
| | | SEM Review | |
| | | Void/Stain | LPD/Residue | Purity |
| RTDC | Void/Stain | 25 | 3 | 89% |
| | LPD/Residue | 1 | 83 | 99% |
| | Accuracy | 96% | 97% | |

| | | Dark Field | | | | BF-DIC |
|---|---|---|---|---|---|---|
| | | Oblique | | Normal | | |
| | DOI | Wide | Narrow | Wide | Narrow | |
| PW | COP | ✓ | ✓ | | | |
| PW | LLPD | ✓ | ✓ | ✓ | ✓ | ✓ |
| EPI | Stacking Fault | ✓ | | | ✓ | |
| SOI | Void/ Stain | ✓ | | | ✓ | |

METHODS AND SYSTEMS FOR IDENTIFYING DEFECT TYPES ON A WAFER

PRIORITY CLAIM

This application claims priority to U.S. Provisional Application No. 60/868,625 entitled "Methods and Systems for Identifying Defect Type," filed Dec. 5, 2006, which is incorporated by reference as if fully set forth herein.

BACKGROUND OF THE INVENTION

1. Field of the Invention

The present invention generally relates to methods and systems for identifying defect types on a wafer. Certain embodiments relate to a computer-implemented method that includes identifying defect types of defects detected on a wafer based on output acquired by a set of different combinations of illumination and collection channels of an inspection system.

2. Description of the Related Art

The following description and examples are not admitted to be prior art by virtue of their inclusion in this section.

Fabricating semiconductor devices such as logic and memory devices typically includes processing a substrate such as a semiconductor wafer using a large number of semiconductor fabrication processes to form various features and multiple levels of the semiconductor devices. For example, lithography is a semiconductor fabrication process that involves transferring a pattern from a reticle to a resist arranged on a semiconductor wafer. Additional examples of semiconductor fabrication processes include, but are not limited to, chemical-mechanical polishing, etching, deposition, and ion implantation. Multiple semiconductor devices may be fabricated in an arrangement on a single semiconductor wafer and then separated into individual semiconductor devices.

Inspection processes are used at various steps during a semiconductor manufacturing process to detect defects on wafers to promote higher yield in the manufacturing process and thus higher profits. Inspection has always been an important part of fabricating semiconductor devices such as integrated circuits (ICs). However, as the dimensions of semiconductor devices decrease, inspection becomes even more important to the successful manufacture of acceptable semiconductor devices because smaller defects can cause the devices to fail. For instance, as the dimensions of semiconductor devices decrease, detection of defects of decreasing size has become necessary since even relatively small defects may cause unwanted aberrations in the semiconductor devices.

Inspection for many different types of defects has also become more important recently. For instance, in order to use inspection results to monitor and correct semiconductor fabrication processes, it is often necessary to know what types of defects are present on a specimen. In addition, since controlling every process involved in semiconductor manufacturing is desirable to attain the highest yield possible, it is desirable to have the capability to detect the different types of defects that may result from many different semiconductor processes. The different types of defects that are to be detected may vary dramatically in their characteristics. For example, defects that may be desirable to detect during a semiconductor manufacturing process may include thickness variations, particulate defects, scratches, pattern defects such as missing pattern features or incorrectly sized pattern features, and many others having such disparate characteristics.

Classifying defects found on wafers and other specimens has, therefore, become increasingly important in order to determine what kinds of defects are present on the wafers in addition to distinguishing defect types of interest from other defect types. Several fully automatic defect classification (ADC) tools are now available. Typically, these tools use classification "recipes" to perform defect classification. A "recipe" can be generally defined as a set of instructions that define an operation to be performed by a tool and that are provided to and run on the tool upon request by a user. Classification recipes are typically generated using previously acquired data for specific defect classes that may be assembled in a suitable database. In the simplest implementation, the ADC tool can then compare unknown defects to those included in the specific defect classes to determine which defect class the unknown defect is most like. Obviously, much more complicated algorithms can be used by the ADC tool to determine the defect class to which the unknown defect most likely belongs.

Sometimes ADC is performed after inspection of a wafer. However, some systems and methods have been developed that can be used to perform ADC during inspection or "on-the-fly." Examples of such systems and methods are illustrated in International Publication No. WO 99/67626 by Ravid et al., which is incorporated by reference as if fully set forth herein. The systems and methods described in this publication are generally configured to separately detect defects in the electrical signals produced by different detectors. In other words, the electrical signals produced by each of the detectors are processed separately to determine if each detector has detected a defect. At any time that a defect is detected in the electrical signals produced by one of the detectors, the electrical signals produced by all of the detectors are analyzed collectively to determine scattered light attributes of the defect such as reflected light intensity, reflected light volume, reflected light linearity, and reflected light asymmetry. The defect is then classified (e.g., as a pattern defect or a particle defect) based on these attributes.

Other currently available inspection systems are configured to inspect a specimen with more than one detection channel, to detect defects on the specimen by separately processing the data acquired by each of the channels, and to classify the defects by separately processing the data acquired by each of the channels. The defects detected by each of the individual channels may also be further processed separately, for example, by generating different wafer maps, each illustrating the defects detected by only one of the individual channels. The results generated by more than one channel of such a system may then be combined using, for example, Venn addition of the individual wafer maps.

Additional examples of systems and methods for classifying anomalies on sample surfaces are illustrated in U.S. Pat. No. 6,590,645 to Chen et al., U.S. Pat. No. 7,016,031 to Chen et al., and U.S. Pat. No. 7,038,772 to Chen et al., which are incorporated by reference as if fully set forth herein. In these systems and methods, two or more defect maps may be provided for the same sample surface at different detection sensitivities and/or processing thresholds. The defect maps may then be compared for better characterization of the anomalies as scratches, area anomalies, or point anomalies. The results from such map(s) can be used to monitor the process conditions to obtain better yield.

The systems and methods described in the above-referenced patents have provided significant advantages for classifying anomalies. Nevertheless, the systems and methods could be improved in a number of ways. For instance, in the systems and methods described in the above-referenced patents, two or more maps of defects detected at different detection sensitivities on a wafer can be used to distinguish the defect types by size, which is advantageous because relatively large size defects will impact the yield of semiconductor devices for a given design dimension. However, this method of finding defects by size is not sufficient to separate all killer defect types from each other and to separate killer defect types that are related to various wafer manufacturing processes.

Examples of systems and methods for a wafer inspection system using multiple angles and multiple wavelength illumination are illustrated in U.S. Pat. No. 6,956,644 to Biellak et al., which is incorporated by reference as if fully set forth herein. As described in this patent, a method for detecting an anomaly on a top surface of a substrate includes directing a first radiation beam having a first wavelength at the top surface of the substrate at a first angle measured from normal and directing a second radiation beam having a second wavelength at the top surface of the substrate at a second angle measured from normal, where the second wavelength is not equal to the first wavelength. The method then includes detecting scattered radiation from the first radiation beam and the second radiation beam to detect the presence of particles or crystal-originated pits (COPs) and to differentiate between the two. Differences in the scattered radiation detected from the first radiation beam and from the second radiation beam provide the data needed to differentiate between particles and COPs.

The systems and methods described in the above-referenced patent have provided significant advantages for wafer inspection. Nevertheless, the systems and methods could be improved in a number of ways. For instance, the methods illuminate wafers at two oblique angles of incidence and different wavelengths. The methods differentiate between COPs and particles using the scattering signal and strength. But this method may be limited to differentiating between COPs and particles. Therefore, this method may not be able to address needs of other defect type classification.

Examples of systems and methods for simultaneous or sequential multi-perspective specimen defect inspection are illustrated in U.S. Pat. No. 6,922,236 to Vaez-Iravani et al., which is incorporated by reference as if fully set forth herein. In this patent, systems and methods for inspecting a surface of a specimen such as a semiconductor wafer are provided. A system may include an illumination system configured to direct a first beam of light to a surface of the specimen at an oblique angle of incidence and to direct a second beam of light to a surface of the specimen at a substantially normal angle. The system may also include a collection system configured to collect at least a portion of the first and second beams of light returned from the surface of the specimen.

The systems and methods described in the above-referenced patent have provided significant advantages for defect inspection. Nevertheless, the systems and methods could be improved in a number of ways. For instance, the defect inspection system for semiconductor wafers described in this patent includes an illumination module with oblique and normal angles and a signal collection module. The patent addresses the hardware design of a defect inspection system, but does not include methodology of how to conduct defect type classification.

Accordingly, it would be advantageous to develop methods and systems for identifying defect types on a wafer that do not have one or more of the disadvantages of the methods and systems described above.

SUMMARY OF THE INVENTION

The following description of various embodiments of methods, carrier media, and systems is not to be construed in any way as limiting the subject matter of the appended claims.

One embodiment relates to a computer-implemented method for identifying defect types on a wafer. The method includes acquiring output of an inspection system for defects detected on a wafer. The output is acquired by different combinations of illumination and collection channels of the inspection system. The method also includes identifying defect types of the defects based on the output acquired by a set of the different combinations. The set of the different combinations is selected based on the defect types to be identified on the wafer and a wafer type of the wafer such that a different set of the different combinations of the illumination and collection channels is used for identifying different defect types on different wafer types.

In one embodiment, the defect types of the defects include one or more yield killing defect types. In another embodiment, the defect types of the defects include defect types other than particles and crystal-originated pits (COPs).

In one embodiment, the set of the different combinations includes all available combinations of the illumination and collection channels of the inspection system. In another embodiment, the set of the different combinations includes a subset of all available combinations of the illumination and collection channels of the inspection system.

In one embodiment, the different combinations included in the set include two or more of a combination of an oblique incidence illumination channel and a wide angle collection channel, a combination of the oblique incidence illumination channel and a narrow angle collection channel, a combination of a normal incidence illumination channel and the wide angle collection channel, and a combination of the normal incidence illumination channel and the narrow angle collection channel.

In another embodiment, the different combinations included in the set include two or more of a combination of an oblique incidence illumination channel and a wide angle collection channel, a combination of the oblique incidence illumination channel and a narrow angle collection channel, a combination of a normal incidence illumination channel and the wide angle collection channel, a combination of the normal incidence illumination channel and the narrow angle collection channel, and a combination of the illumination and collection channels configured for bright field (BF) differential interference contrast (DIC).

In one embodiment, the output acquired for the defects by at least one of the different combinations included in the set is responsive to light scattered from the defects. In another embodiment, identifying the defect types includes identifying the defect types of the defects based on characteristics of the output, and the characteristics include scattering angle and intensity. In an additional embodiment, identifying the defect types includes identifying the defect types of the defects based on uniqueness of the output acquired for one of the defect types by one of the different combinations included in the set compared to the output acquired for the one of the defect types by another of the different combinations included in the set.

In one embodiment, identifying the defect types includes identifying the defect types of the defects based on ratios of scattering signal intensity of the output acquired for the defects by the different combinations included in the set. In another embodiment, identifying the defect types includes identifying the defect types of the defects based on a function of different reported sizes for the defects, and the different reported sizes for the defects are separately determined from the output acquired by the different combinations included in the set. In an additional embodiment, identifying the defect types includes determining a function of different reported sizes for the defects separately determined from the output acquired by the different combinations included in the set and using the function as an attribute for rule based binning.

In one embodiment, the output acquired by the set of the different combinations includes defect characteristics acquired by BF DIC. In another embodiment, the method includes subtracting defects commonly detected by the different combinations included in the set from the defects detected on the wafer prior to identifying the defect types.

In one embodiment, the wafer types include polished silicon wafers, annealed silicon wafers, epitaxial wafers, and silicon-on-insulator (SOI) wafers. In another embodiment, the inspection system is configured as an unpatterned wafer inspection system. In some embodiments, the method is performed automatically.

Each of the steps of each of the embodiments of the method described above may be further performed as described further herein. In addition, each of the embodiments of the method described above may include any other step(s) of any other method(s) described herein. Furthermore, each of the embodiments of the method described above may be performed by any of the systems described herein.

Another embodiment relates to a carrier medium that includes program instructions executable on a computer system for performing a computer-implemented method for identifying defect types on a wafer. The computer-implemented method includes acquiring output of an inspection system for defects detected on a wafer. The output is acquired by different combinations of illumination and collection channels of the inspection system. The computer-implemented method also includes identifying defect types of the defects based on the output acquired by a set of the different combinations. The set of the different combinations is selected based on the defect types to be identified on the wafer and a wafer type of the wafer such that a different set of the different combinations of the illumination and collection channels is used for identifying different defect types on different wafer types.

The carrier medium described above may be further configured as described herein. The steps of the computer-implemented method may be performed as described further herein. In addition, the computer-implemented method for which the program instructions are executable may include any other step(s) of any other method(s) described herein.

An additional embodiment relates to a system configured to identify defect types on a wafer. The system includes an optical subsystem configured to acquire output for defects on a wafer. The output is acquired by different combinations of illumination and collection channels of the optical subsystem. The system also includes a computer system configured to identify defect types of the defects based on the output acquired by a set of the different combinations. The set of the different combinations is selected based on the defect types to be identified on the wafer and a wafer type of the wafer such that a different set of the different combinations of the illumination and collection channels is used for identifying different defect types on different wafer types. The embodiment of the system described above may be further configured as described herein.

BRIEF DESCRIPTION OF THE DRAWINGS

Further advantages of the present invention may become apparent to those skilled in the art with the benefit of the following detailed description of the preferred embodiments and upon reference to the accompanying drawings in which:

FIG. 7 is a schematic diagram illustrating examples of scattering patterns for different defect types illuminated by different illumination channels of an embodiment of an inspection system described herein;

FIG. 8 is a schematic diagram illustrating examples of scattering patterns for a COP illuminated by an oblique incidence illumination channel of an embodiment of an inspection system described herein;

FIG. 9 is a table illustrating classification accuracy and purity results for identifying COP defect types separately from light point defect (LPD) and scratch defect types using output acquired by a set of the different combinations shown in FIG. 2;

FIG. 12 includes images of examples of an LLPD air pocket defect and an LLPD polishing defect;

FIG. 13 is a schematic diagram illustrating a set of wafer maps showing defects detected by dark field (DF) using both oblique and normal incidence, defects detected by BF DIC, and defects detected by both DF and BF DIC;

FIG. 14 is a table illustrating classification accuracy and purity results for identifying LLPD defect types separately from LPD defect types using output acquired by a set of different combinations including DF both oblique and normal incidence and BF DIC;

Figure 1:
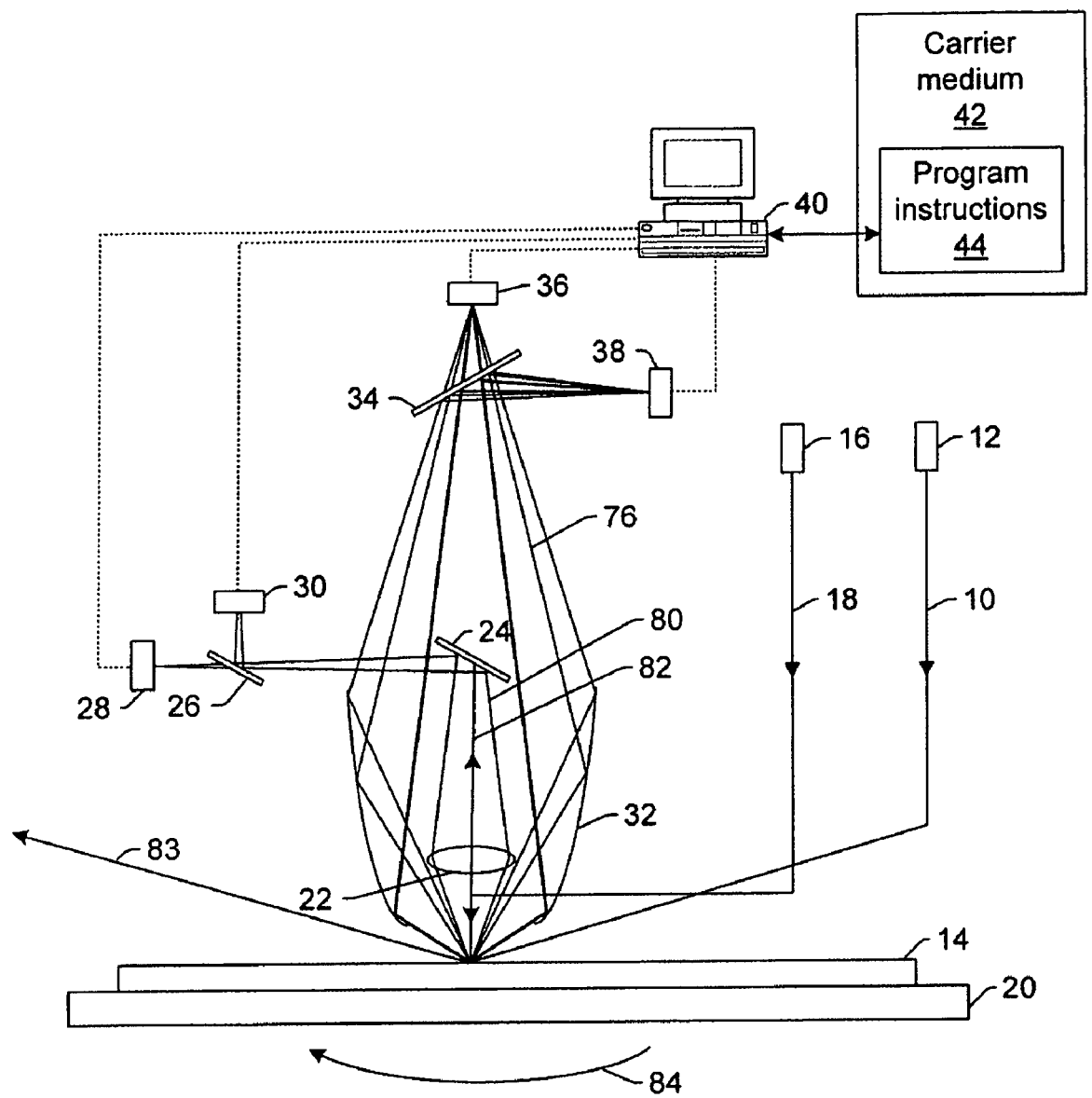
FIG. 1 is a schematic diagram illustrating a side view of one embodiment of a system configured to identify defect types on a wafer and one embodiment of a carrier medium that includes program instructions executable on a computer system for performing a computer-implemented method for identifying defect types on a wafer.

While the invention is susceptible to various modifications and alternative forms, specific embodiments thereof are shown by way of example in the drawings and may herein be described in detail. The drawings may not be to scale. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

As used herein, the term "specimen" generally refers to a wafer or any other specimen on which defects of interest (DOI) may be located. Although the terms "specimen" and "wafer" are used interchangeably herein, it is to be understood that embodiments described herein with respect to a wafer may configured and/or used for any other specimen (e.g., a reticle, mask, or photomask).

As used herein, the term "wafer" generally refers to substrates formed of a semiconductor or non-semiconductor material. Examples of such a semiconductor or non-semiconductor material include, but are not limited to, monocrystalline silicon, gallium arsenide, and indium phosphide. Such substrates may be commonly found and/or processed in semiconductor fabrication facilities.

One or more layers may be formed upon a wafer. Many different types of such layers are known in the art, and the term wafer as used herein is intended to encompass a wafer on which all types of such layers may be formed. One or more layers formed on a wafer may be patterned. For example, a wafer may include a plurality of dies, each having repeatable patterned features. Formation and processing of such layers of material may ultimately result in completed semiconductor devices. As such, a wafer may include a substrate on which not all layers of a complete semiconductor device have been formed or a substrate on which all layers of a complete semiconductor device have been formed.

The wafer may further include at least a portion of an integrated circuit (IC), a thin-film head die, a micro-electromechanical system (MEMS) device, flat panel displays, magnetic heads, magnetic and optical storage media, other components that may include photonics and optoelectronic devices such as lasers, waveguides and other passive components processed on wafers, print heads, and bio-chip devices processed on wafers.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

One embodiment of a system that is configured to identify defect types on a wafer is illustrated in FIG. 1. The system shown in FIG. 1 is configured for unpatterned wafer inspection and is based on the SP1-TBI system, which is commercially available from KLA-Tencor, San Jose, Calif. This inspection system is described in more detail in U.S. Pat. No. 6,538,730 to Vaez-Iravani et al., which is incorporated by reference as if fully set forth herein. The system shown in FIG. 1 may be further configured as described in this patent for patterned and unpatterned wafer inspection. For the sake of clarity, some of the components and details of the system have been omitted from FIG. 1 and the corresponding description presented herein. In addition, U.S. Pat. No. 6,538,730 is related to U.S. Pat. No. 6,201,601 to Vaez-Iravani et al. and U.S. Pat. No. 6,271,916 to Marxer et al., which are also incorporated by reference as if fully set forth herein. The system shown in FIG. 1 may be further configured as described in these patents.

The system shown in FIG. 1 includes an optical subsystem configured to acquire output for defects on a wafer. The output is acquired by different combinations of illumination and collection channels of the optical subsystem. The optical subsystem includes two illumination channels. One illumination channel is configured to generate light 10. For instance, the illumination channel may include light source 12, which is configured to generate light 10. The illumination channel is configured to direct light 10 to wafer 14 at an oblique angle of incidence. Therefore, this illumination channel is an oblique incidence illumination channel. The illumination channel may include a number of optical components (not shown) positioned in the path of light 10 such as folding mirror(s), beam splitter(s), polarizing component(s), filter(s), and lenses. The angle of incidence may vary depending on, for example, the characteristics of the light and the characteristics of the wafer. One suitable angle of incidence may be about 70° from normal to the upper surface of the wafer.

The optical subsystem also includes another illumination channel, which includes light source 16. Light source 16 is configured to generate light 18, which is directed by the illumination channel to wafer 14 at a substantially normal angle of incidence. Therefore, this illumination channel is configured as a normal incidence illumination channel. The illumination channel may include a number of optical components (not shown) positioned in the path of light 18. These optical components may include any of those described above.

Light sources 12 and 16 may include any suitable light sources known in the art such as lasers. In a different embodiment, the system may include a single light source (not shown) that is used to provide light for both oblique and normal illumination. For example, a single light source such as a multi-wavelength laser may be coupled to a beam splitter (not shown). The beam splitter may be configured to split the light from the laser into separate beams having different wavelengths, one of which is used for normal illumination and the other of which is used for oblique illumination. The illumination channels may include any other suitable combination of a single light source and beam multiplier(s) known in the art. In any of the above embodiments, light 10 may have one or more characteristics such as wavelength and/or polarization that are different than the characteristics of light 18. Alternatively, light 10 may have substantially the same characteristics as light 18.

Wafer 14 is supported on stage 20, which may be rotated and translated such that light 10 and 18 illuminates an area or spot on the wafer that moves in a spiral path. Alternatively, light 10 and 18 may be scanned over the wafer in any manner known to those skilled in the art to trace the spiral path or another type of scan path across the wafer.

Illumination of the wafer will cause scattering of the light from the wafer. In addition, both oblique incidence light and normal incidence light may be scattered from the wafer. The optical subsystem shown in FIG. 1 includes a detection subsystem that is configured to collect and detect light scattered from the wafer (e.g., light scattered from defects on the wafer) and to generate output responsive to the scattered light. The output can be used to detect defects on the wafer as described further herein.

The detection subsystem includes two different collection channels. One collection channel includes lens collector 22, mirror 24, beam splitter 26, and detectors 28 and 30, which form a "narrow" angle collection channel (also referred to herein as the "narrow" channel) of the detection subsystem. In other words, light scattered from the illuminated area on the wafer along directions relatively close to normal to the surface of the wafer is collected and focused by lens collector 22. In this manner, lens collector 22 collects light scattered from the wafer at relatively "narrow" scattering angles. Lens collector 22 directs the collected light to mirror 24, which directs the light to beam splitter 26. Beam splitter 26 is configured to direct one portion of the light to detector 28 and the other portion of the light to detector 30. One detector is used to detect light scattered at relatively narrow angles due to illumination by the normal incidence beam, and the other detector is used to detect light scattered at relatively narrow angles due to illumination by the oblique incidence beam. Therefore, the narrow channel is configured as a dark field (DF) channel. Detectors 28 and 30 may include any suitable detectors known in the art (e.g., photomultiplier tubes (PMTs)). In addition, detectors 28 and 30 may be similarly or differently configured. The narrow angle collection channel of the detection subsystem may include any other optical components (not shown) known in the art. For example, one or more polarizing components may be placed in the path of the collected light. In addition, a spatial filter may be included in the narrow angle collection channel of the detection subsystem to prevent specular reflection of the normal incidence beam from reaching detectors 28 and 30.

Another collection channel of the detection subsystem includes ellipsoidal mirror 32, beam splitter 34, and detectors 36 and 38, which form a "wide" angle collection channel (also referred to herein as the "wide" channel) of the detection subsystem. In other words, light scattered from the illuminated area on the wafer along directions relatively far from normal to the surface of the wafer is collected and focused by ellipsoidal mirror 32. In this manner, ellipsoidal mirror 32 collects light scattered from the wafer at relatively "wide" scattering angles. Ellipsoidal mirror 32 directs the collected light to beam splitter 34. Beam splitter 34 is configured to direct one portion of the light to detector 36 and the other portion of the light to detector 38. One detector is used to detect light scattered at relatively wide angles due to illumination by the normal incidence beam, and the other detector is used to detect light scattered at relatively wide angles due to illumination by the oblique incidence beam. Therefore, the wide channel is configured as a DF channel. Detectors 36 and 38 may include any suitable detectors known in the art (e.g., PMTs). In addition, detectors 36 and 38 may be similarly or differently configured. The wide angle collection channel of the detection subsystem may include any other optical components (not shown) known in the art. For example, one or more polarizing components may be placed in the path of the collected light.

In some embodiments, the optical subsystem shown in FIG. 1 is configured to include a combination (not shown) of the illumination and collection channels configured for bright field (BF) differential interference contrast (DIC). The combination of the illumination and collection channels configured for BF DIC may be further configured as described herein.

Detectors 28, 30, 36, and 38 are configured to generate output responsive to the scattered light. The system also includes computer system 40. Computer system 40 is coupled to detectors 28, 30, 36, and 38 by transmission media as shown by the dotted lines in FIG. 1. The transmission media may include any suitable transmission media known in the art. In addition, one or more additional components (not shown) may be interposed between the detectors and the computer system such as analog-to-digital converters. In this manner, output generated by the detectors can be sent to the computer system. The computer system may be configured to use the output to detect defects oil the wafer. The computer system may be configured to use any algorithm and/or method known in the art for detecting the defects using the output.

The computer system is configured to identify defect types of the defects based on the output acquired by a set of the different combinations. The set of the different combinations is selected based on the defect types to be identified on the wafer and a wafer type of the wafer such that a different set of the different combinations of the illumination and collection channels is used for identifying different defect types on different wafer types. The computer system may be configured to identify the defect types according to any embodiments described further herein. The set of the different combinations may include any of the embodiments of the sets described further herein. In addition, the set of the different combinations may be selected according to any of the embodiments described further herein.

The computer system may include any suitable computer system known in the art. For example, computer system 40 may take various forms, including a personal computer system, mainframe computer system, workstation, image computer, parallel processor, or any other device known in the art. In general, the term "computer system" may be broadly defined to encompass any device having one or more processors, which executes instructions from a memory medium.

Carrier medium 42, shown in FIG. 1, includes program instructions 44 executable on computer system 40 for performing one or more of the computer-implemented methods described herein. For example, program instructions 44 are executable on computer system 40 for performing a computer-implemented method for identifying defect types on a wafer. The computer-implemented method includes acquiring output of an inspection system for defects detected on a wafer. The output is acquired by different combinations of illumination and collection channels of the inspection system. Acquiring the output may be performed according to any of the embodiments described herein. The different combinations of the illumination and collection channels may include any of the combinations of any of the illumination and collection channels described herein.

The computer-implemented method also includes identifying defect types of the defects based on the output acquired by a set of the different combinations. The set of the different combinations is selected based on the defect types to be identified on the wafer and a wafer type of the wafer such that a different set of the different combinations of the illumination and collection channels is used for identifying different defect types on different wafer types. Identifying the defect types may be performed according to any of the embodiments described herein. The set of the different combinations may include any of the sets of the different combinations described herein. In addition, the set of the different combinations may be selected according to any of the embodiments described herein.

Program instructions 44 implementing methods such as those described herein may be transmitted over or stored on carrier medium 42. The carrier medium may be a transmission medium such as a wire, cable, or wireless transmission link. The carrier medium may also be a storage medium such as a read-only memory, a random access memory, a magnetic or optical disk, or a magnetic tape.

The program instructions may be implemented in any of various ways, including procedure-based techniques, component-based techniques, and/or object-oriented techniques, among others. For example, the program instructions may be implemented using Matlab, Visual Basic, ActiveX controls, C, C++ objects, C#, JavaBeans, Microsoft Foundation Classes ("MFC"), or other technologies or methodologies, as desired.

As described above, the program instructions may be executable on computer system 40. Therefore, the program instructions may be executable on a computer system coupled to or included in an inspection system. However, the program instructions may be executable on a computer system that is not coupled to or included in an inspection system. In this manner, the carrier medium and the computer system may be configured as a "stand alone" system. The stand alone system may, however, be configured to acquire the output described above (e.g., from a processor or storage medium in which an inspection system stored the output). The stand alone system may acquire the output in any manner known in the art (e.g., via a transmission medium that may include "wired" and/or "wireless" portions). In this manner, the transmission medium may serve as a data link between the computer system and the system or storage medium from which the output is acquired. Therefore, the methods described herein may or may not include acquiring output for defects detected on a wafer (e.g., output responsive to light scattered (and possibly output responsive to light specularly reflected) by the defects) by performing inspection of a wafer. In other words, the methods described herein may be performed by a system that does not include an inspection system.

The system embodiments described herein may also or alternatively be coupled to another system such as a review system, an analysis system (e.g., an electron dispersive x-ray spectroscopy (EDX) system), a metrology system, a process tool such as a process tool configured to form a wafer, a polishing tool, a cleaning tool, a plating tool, a deposition tool, a thermal growth tool, an anneal tool, an epitaxial (EPI) tool, an ion implantation tool, an etch tool, and the like. The system embodiments described herein may be coupled to the other system in any suitable manner (e.g., by a transmission medium such as one of those described above, by forming a part of the other system, by being physically coupled to the other system, etc.).

Another embodiment relates to a computer-implemented method for identifying defect types on a wafer. The computer-implemented method includes acquiring output of an inspection system for defects detected on a wafer. For example, the method may include acquiring the output from a computer system of the inspection system or a storage medium in which the inspection system stored the output (e.g., a storage medium of the inspection system, a fab database, etc.). In this manner, the method may not include inspecting the wafer. However, acquiring the output may include inspecting the wafer, which may be performed as described herein. The output of the inspection system acquired and used in the method may have any suitable format (e.g., a KLARF file). The inspection system may be configured according to any of the embodiments described herein.

The output is acquired by different combinations of illumination and collection channels of the inspection system. In this manner, the output may vary depending on the configuration of the inspection system. For example, as described above, the inspection system may include an oblique incidence illumination channel and a normal incidence illumination channel. In addition, the inspection system includes a wide angle collection channel and a narrow angle collection channel. Therefore, the different combinations of illumination and collection channels of this inspection system that acquire output for the wafer (and therefore defects on the wafer) include a combination of the oblique incidence illumination channel and the wide angle collection channel, a combination of the oblique incidence illumination channel and the narrow angle collection channel, a combination of the normal incidence illumination channel and the wide angle collection channel, and a combination of the normal incidence illumination channel and the narrow angle collection channel. In addition, the inspection system may include different illumination wavelength and collector configurations at discrete locations. As described further herein, such an inspection system may also include a combination of an illumination channel and a collection channel configured for BF DIC. Therefore, output for the wafer (and therefore defects on the wafer) may also be acquired by the inspection system in a BF DIC mode.

The method also includes identifying defect types of the defects based on the output acquired by a set of the different combinations. The set of the different combinations is selected based on the defect types to be identified on the wafer and a wafer type of the wafer such that a different set of the different combinations of the illumination and collection channels is used for identifying different defect types on different wafer types. The different wafer types may include any of the wafer types described herein. For example, in one embodiment, the wafer types include polished silicon (Si) wafers (PW), annealed Si wafers, epitaxial (EPI) wafers, and silicon-on-insulator (SOI) wafers. The output may be acquired for the wafer (and therefore defects on the wafer) by all available combinations of the illumination and collection channels of the inspection system although the output that is used to identify the defect types of the defects will vary depending on the defect types being identified on the wafer and the wafer type of the wafer.

In this manner, the embodiments described herein may include essentially combining or otherwise collectively processing output acquired using multiple illumination and scattered light channels to identify semiconductor defect types. In one embodiment, the method is performed automatically (e.g., without input from a user). In this manner, the defect types may be identified automatically by the embodiments described herein. In addition, acquiring the output and identifying the defect types may be performed as the wafer is being inspected (e.g., in a run time mode). Alternatively, acquiring the output and identifying the defect types may be performed after the wafer is inspected. In this manner, defect classification may or may not be performed by the embodiments described herein in a run time mode or "on-the-fly."

In one embodiment, the inspection system is configured as an unpatterned wafer inspection system. Therefore, the embodiments may be used for identifying unpatterned wafer defect types. In particular, the methods and systems described herein may utilize output generated by a set of different combinations of multiple illumination (e.g., laser illumination) channels and multiple collection channels of an unpatterned defect inspection system such as that described above. The configuration of multiple collection channels may include wide and narrow collection channels for the DF incidence. In one embodiment, the different combinations included in the set include two or more of a combination of an oblique incidence illumination channel and a wide angle collection channel, a combination of the oblique incidence illumination channel and a narrow angle collection channel, a combination of a normal incidence illumination channel and the wide angle collection channel, and a combination of the normal incidence illumination channel and the narrow angle collection channel. The described technology may include DF and BF DIC technology. In another embodiment, the different combinations included in the set include two or more of a combination of an oblique incidence illumination channel and a wide angle collection channel, a combination of the oblique incidence illumination channel and a narrow angle collection channel, a combination of a normal incidence illumination channel and the wide angle collection channel, a combination of the normal incidence illumination channel and the narrow angle collection channel, and a combination of the illumination and collection channels configured for BF DIC.

In one embodiment, the output acquired for the defects by at least one of the different combinations included in the set is responsive to light scattered from the defects. In this manner, in some embodiments, at least one of the different combinations included in the set includes a combination for DF defect detection. For example, the method may include comparing defect detection performed by scanning a wafer using normal and oblique incidence illumination and wide and narrow collection channels. Furthermore, the embodiments described herein may use output acquired by at least one channel that detects light scattered from defects on a wafer and at least one channel that detects light specularly reflected from the defects on the wafer. For example, the embodiments described herein may use one or more characteristics of light detected by a first DF channel and a second DF channel to identify different defects types on a wafer type. However, the embodiments described herein may also use one or more characteristics of light detected by a DF channel and one or more characteristics of light detected by a BF channel (e.g., a BF DIC channel) to identify different defect types detected on a wafer type. In this manner, the embodiments can classify defects based on characterization of defect detection across various illumination incidence angles and collection channels.

Figure 2:
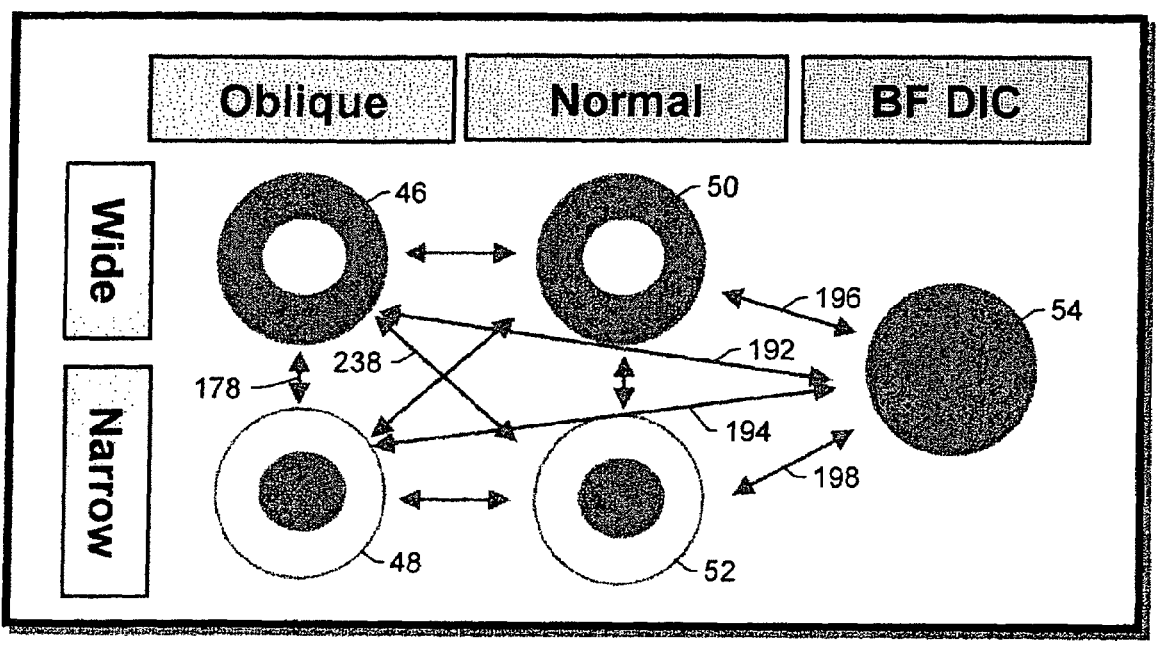
FIG. 2 is a schematic diagram illustrating various embodiments of sets of different combinations of illumination and collection channels of an inspection system, output acquired by which can be used in the embodiments described herein to identify crystal-originated pits (COPs) and large light point defect (LLPD) types on polished wafers (PW), stacking fault (SF) defect types on EPI wafers, and void defect types on silicon-on-insulator (SOI) wafers.

In one embodiment, the set of the different combinations includes all available combinations of the illumination and collection channels of the inspection system. For example, the set of the different combinations may include all combinations of the illumination and collection channels included in the inspection system. Therefore, the embodiments described herein allow a comparison between output acquired by all of the combinations of available illumination angles and collector locations to separate defect types. The methods can also be used to build a methodology that allows comparing output (e.g., data and/or signals) acquired by all of the combinations of illumination angles and collector locations to separate defect types. In another embodiment, the set of the different combinations includes a subset of all available combinations of the illumination and collection channels of one embodiment of the inspection system. For example, FIG. 2 illustrates various sets of the different combinations, output acquired by which can be used in the embodiments described herein for one embodiment of an inspection system. In particular, as shown in FIG. 2, the different combinations include a combination of an oblique incidence illumination channel and a wide angle collection channel ("oblique wide" 46), a combination of the oblique incidence illumination channel and a narrow angle collection channel ("oblique narrow" 48), a combination of a normal incidence illumination channel and the wide angle collection channel ("normal wide" 50), a combination of the normal incidence illumination channel and the narrow angle collection channel ("normal narrow" 52), and a BF DIC combination ("BF DIC" 54). The output acquired by each of the different combinations may be separately used to detect defects on the wafer in any suitable manner.

The arrows shown in FIG. 2 illustrate different sets that can be used in embodiments described herein. In particular, as shown in FIG. 2, each of the different combinations shown in FIG. 2 can be included in a set with each of the other different combinations shown in FIG. 2. For example, oblique wide 46 may be included in a set with oblique narrow 48, normal wide 50, normal narrow 52, or BF DIC 54. In addition, oblique narrow 48 may be included in a set with normal wide 50, normal narrow 52, or BF DIC 54. Furthermore, normal wide 50 may be included in a set with normal narrow 52 or BF DIC 54. Moreover, normal narrow 52 may be included in a set with BF DIC 54. In addition, each of the sets may include two or more of the different combinations (e.g., a set may include oblique wide 46, oblique narrow 48, and normal wide 50). As described further herein, the output acquired by the different combinations in a set may be compared or otherwise processed collectively to identify defect types on the wafers. Therefore, in some embodiments, the output acquired by each of the different combinations of illumination and collection channels of an inspection system can be compared to the output acquired by each of the other different combinations to identify defect types on a wafer.

In one embodiment, identifying the defect types includes identifying the defect types of the defects based on characteristics of the output, and the characteristics include scattering angle and intensity. For example, due to the nature of defect shapes, dimensions, and materials, substrate chemical composition, and illumination angles, the scattering angle and intensity of light scattered from different defect types may vary. The discretization of scattering angle and intensity provides an opportunity to identify the types of defects detected on various wafer types at various process steps. In particular, the discretization of scattering angle and intensity by multiple illumination and collection channels can be used to identify the types of defects on various wafer types. This method of defect type identification and separation may not only be predicted by simulation results, but also has been verified by empirical data collected from various wafer types (e.g., PW, annealed Si wafers, EPI wafers, and SOI wafers).

In one embodiment, identifying the defect types includes identifying the defect types of the defects based on uniqueness of the output acquired for one of the defect types by one of the different combinations included in the set compared to the output acquired for the one of the defect types by another of the different combinations included in the set. Therefore, the embodiments can identify the defect types by the uniqueness defects show in certain collection channel(s), but not in other channel(s). For example, based on the scattering intensity in different collectors, the method may identify the defect types by the uniqueness of light scattering by defects shown in certain collection channel(s), but not in other channel(s).

In one embodiment, identifying the defect types includes identifying the defect types of the defects based on ratios of scattering signal intensity of the output acquired for the defects by the different combinations included in the set. In this manner, the method may include identifying the defect types by ratio of scattering intensity (i.e., signal size) in different collectors. The method may also provide a flexible methodology which can be used for existing and new processes as well as various wafer types for identifying the defect types by the uniqueness of defects shown in certain collection channels, but not in other channels, and the ratio of scattering intensity (e.g., signal size) in different collectors.

In another embodiment, identifying the defect types includes identifying the defect types of the defects based on a function of different reported sizes for the defects, and the different reported sizes for the defects are separately determined from the output acquired by the different combinations included in the set. For example, the reported size determined using output acquired by collection channels is correlated to scattering signal intensity detected by the collection channels. Therefore, based on the scattering intensity in different collection channels, the method may identify the defect types by a function such as the ratio of reported sizes for the common defects (e.g., defects commonly detected by two or more or all of the different combinations included in the set) determined using output acquired by different collection channels. In another example, the function of the different reported sizes for the defects may include vertical or horizontal line functions as well as polynomial curve functions to describe relations between defects' sizing reported by different combinations to identify a defect type. The reported sizes may be determined in any suitable manner.

In addition, the characteristic(s) of light scattered from the defects that are used to identify different defect types on different wafer types may include any of the measurable characteristic(s) of the light such as one or more characteristics of the intensity of the light scattered from the defects and/or one or more characteristics of the scattering patterns of the light scattered from the defects. Different characteristic(s) of the scattered light may be used to identify different defect types on different wafer types. In an additional embodiment, the output acquired by the set of the different combinations includes defect characteristics acquired by BF DIC.

The defect types that are identified by the embodiments described herein may include any of the defect types described herein. For example, in one embodiment, the defect types of the defects include one or more yield killing defect types. In addition, the embodiments described herein may be applied to identify (e.g., automatically identify) yield killing defect types on semiconductor wafers. In another embodiment, the method can be performed by a defect inspection system to identify (e.g., automatically identify) yield killing defect types on semiconductor wafers. For example, the embodiments described herein demonstrate excellent separation between particles and DOI defect types on PW such as large light point defects (LLPD), on EPI wafers (e.g., EPI stacking faults (ESF), and on SOI wafers (e.g., voids)).

In another embodiment, the defect types of the defects include defect types other than particles and crystal-originated pits (COPs). In particular, although the embodiments described herein may be used to identify defect types including particle and COP defect types, the embodiments described herein can also be used to identify other defect types. In other words, the embodiments described herein may include identifying particle and COP defect types, but the embodiments described herein are not limited to identifying just those defect types. In contrast, some previously used methods of defect type classification are limited to the classification of COPs from particles. COPs are surface breaking defects in semiconductor wafers. Although such defect types are important to identify on wafers, such methods have not addressed many needs of other defect type classification. Therefore, the embodiments described herein provide a flexible methodology that can be used for existing and new processes as well as various wafer types. In addition, one advantage of the embodiments described herein is that they provide a flexible methodology that can be used to identify the maximum number of types of defects for existing and new processes and different wafer types. For example, the set of the different combinations is selected based on the defect types to be identified on the wafer and a wafer type of the wafer such that a different set of the different combinations of the illumination and collection channels is used for identifying different defect types on different wafer types. The method may include selecting the DF incidence angles (oblique and/or normal), the DF collection angles (wide and/or narrow), DIC (BF) illumination, or some combination thereof.

The embodiments described herein, therefore, utilize specific classification and detection methods (e.g., specific combinations of channels for specific defect types) to identify defect types of interest on wafer types such as those described above. The embodiments described herein are also advantageously flexible in the channels that can be used for different defect types and different wafer types. For example, the embodiments described herein may be used to differentiate between first and second defect types on a first wafer type and to differentiate between third and fourth defect types on a second wafer type (e.g., where at least one of the first and second defect types is different than at least one of the third and fourth defect types and the first wafer type is different than the second wafer type). In this manner, the embodiments described herein can be used to classify different types of defects detected on one wafer type and to classify other different types of defects detected on another wafer type. In particular, the sets of different combinations of channels, output acquired by which is used to identify different defect types on different wafer types, may be different.

The embodiments also advantageously provide significant flexibility in the channels and the one or more characteristics of the light scattered from defects that are used to identify different defect types on different wafer types. For instance, output acquired by only a subset of different combinations of illumination and collection channels and/or different characteristic(s) of the light scattered from the defects that are available for use in the embodiments described herein may be selected for identification of particular defect types on a particle wafer type. The subset of the different combinations of channels and/or different characteristic(s) may include any of those described herein and may be selected based on the application in which the embodiments are being used (e.g., based on the DOI for a wafer type being inspected and other defects that are not of interest but that may be detected during inspection of that wafer type). The subset of the different combinations of channels and/or different characteristic(s) that are selected for any particular application may be selected by a user. The embodiments may also assist the user in selection of the subset of the different combinations of channels and/or different characteristic(s), for example, by suggesting different combinations of channels and/or characteristic(s) to be used for an application selected by the user or by providing feedback to the user after selections have been made by the user and prior to performing the detection and/or classification. As such, the embodiments described herein may be advantageously used in a number of applications for identification or classification of dramatically different defect types on dramatically different wafer types. Therefore, the embodiments described herein provide significant value to potential users of the applications since one system, method, or carrier medium may be used for different defect types and different wafer types instead of multiple systems, methods, and carrier media.

Figure 3:
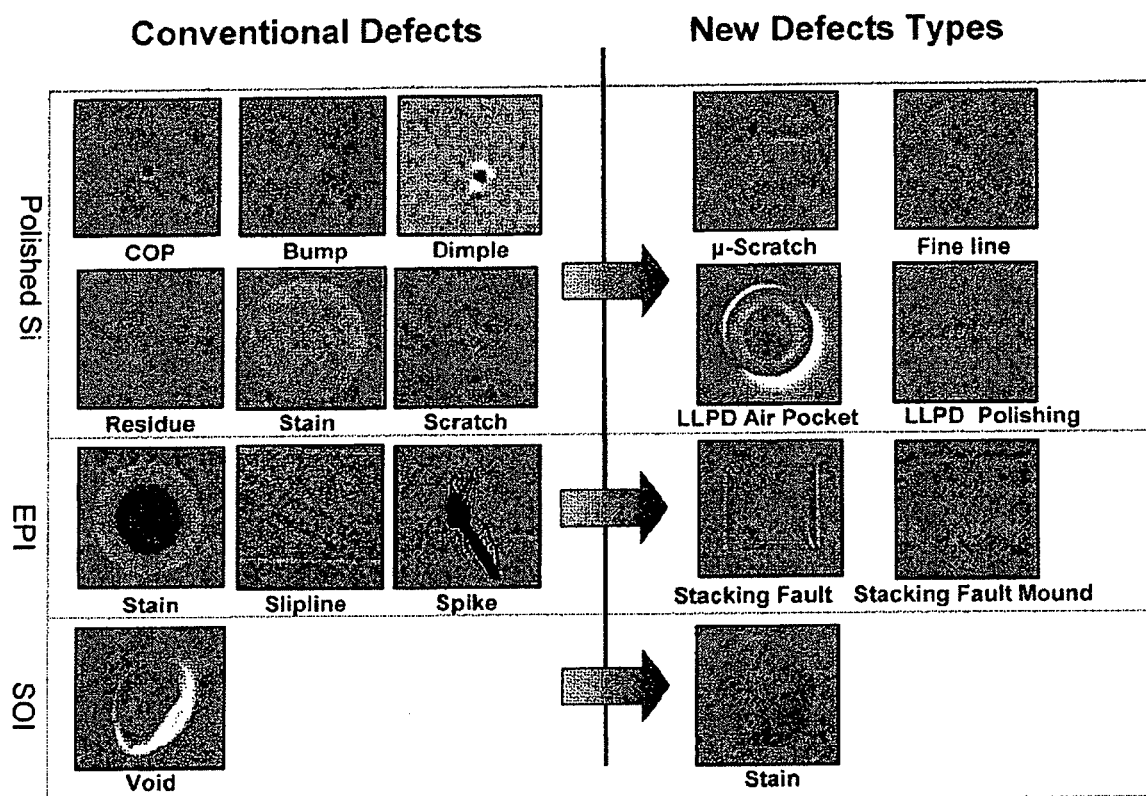
FIG. 3 includes images of examples of different defect types of defects of interest (DOI) for different wafer types.

The embodiments described herein can be used in various applications and implementations. For example, there are new challenges for IC incoming quality control (IQC) and wafer suppliers for defect sensitivity at the 45 nm technology node. In particular, besides the demand for increased sensitivity as a result of the introduction of emerging technology in device fabrication processes, more defects are being discovered that impact device yield and defects near surface or surface roughness become important. For example, on polished Si wafers, conventional DOI (that can be detected by DF oblique mode) include COPs, bumps, dimples, residue, stains, and scratches. In contrast, for polished Si wafers, emerging DOI or new defect types (which may require new modes of detection and may require oblique, normal, and BF illumination for efficient classification) include microscratches, fine-line defects, LLPD air pocket defects, and LLPD polishing defects. In another example, on EPI wafers, conventional DOI (that can be detected by DF oblique mode) include stains, slip-line defects, and spike defects. In contrast, for EPI wafers, emerging DOI (which may require new modes of detection and may require oblique, normal, and BF illumination for efficient classification) include SF defects and SF mound defects. In an additional example, for SOI wafers, conventional DOI (that can be detected by DF oblique mode) include void defects while emerging DOI (which may require new modes of detection and may require oblique, normal, and BF illumination for efficient classification) include stain defects. Images of examples of the DOI described above are illustrated in FIG. 3.

Figure 4:
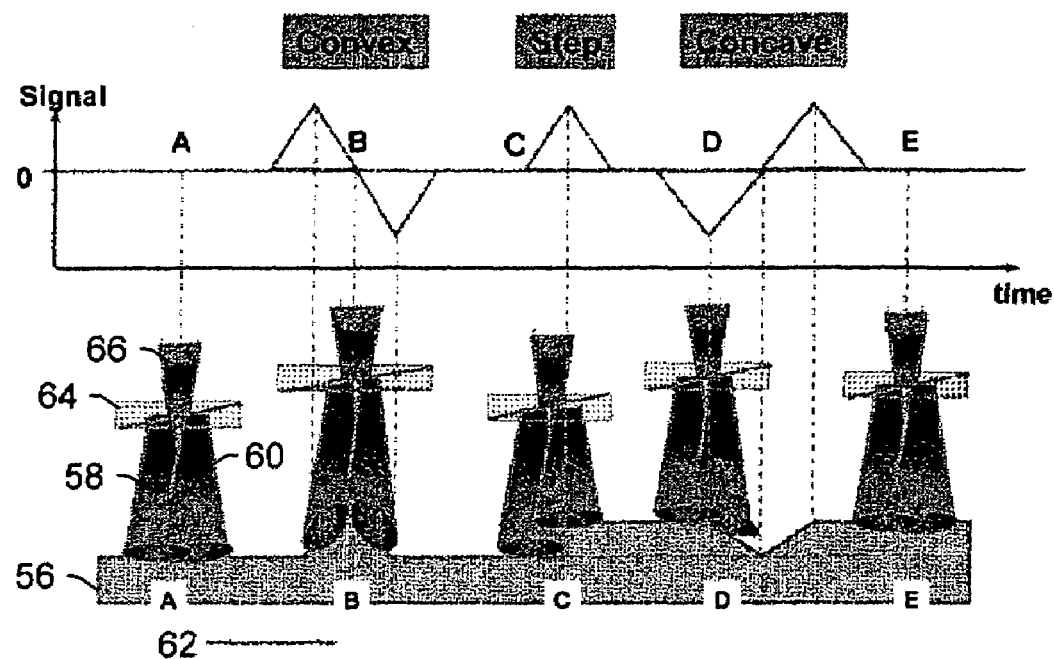
FIG. 4 is a schematic diagram illustrating a side view of one example of a wafer surface and output that may be acquired by bright field (BF) differential interference contrast (DIC) for various points on the wafer surface.

BF illumination-based inspection and/or classification may use DIC technology in which phase difference reveals height or slope information, which can be used to identify relatively low spatial frequency defects that are relatively large, flat, or shallow and may not be detected by DF. FIG. 4 illustrates wafer surface 56 and output (signals) that may be acquired by BF DIC for various points on the wafer surface. The wafer surface shown in FIG. 4 is an arbitrary wafer surface having different topography at points A, B, C, D, and E across the wafer surface. BF DIC may be performed by scanning beams 58 and 60 across wafer surface 56 in direction 62. Beams 58 and 60 reflected from wafer surface 56 pass through prism 64 (e.g., a Nomarski prism or another suitable prism), which is configured to combine orthogonal wavefronts thereby generating beam 66, which may pass through an analyzer (not shown). The analyzer is configured to pass only those components parallel to the transmission azimuth of the analyzer. The parallel wavefronts that pass through the analyzer are able to interfere with each other thereby producing interference that can be detected by a detector (not shown).

As shown in FIG. 4, the output (signal) that would be generated as a function of time as the beams scan across the wafer surface varies depending on the topography of the wafer surface. In particular, portions of the wafer surface that are substantially planar, portions of the wafer surface that have a convex topography, portions of the wafer surface that have a step topography, and portions of the wafer surface having a concave topography produce different BF DIC signals. Therefore, these portions of the wafer surface can be distinguished from one another using the BF DIC signals. As such, output generated by BF DIC may be used to determine height or slope information about wafer surfaces, which can be used to identify relatively low spatial frequency defects that are relatively large, flat, or shallow and may not be detected by DF.

One key role in IC IQC is defining yield relevant defect sensitivity in wafer substrates. However, there is a balance between substrate cost and device performance and yield. The substrates that may be inspected for IC IQC include any of the substrates described herein (e.g., PW, EPI wafers, and SOI wafers). Embodiments described herein may be used for screening and classifying yield killer defects and may provide better IQC. Wafer manufacturers also demand a production final outgoing inspection solution. The inspection solution should be able to detect all DOI to ensure wafer quality, include a single inspection step (e.g., no additional "decorated" or destructive steps to identify relatively small defect types), provide improved defect classification efficiency for early detection of correctable process root causes, and be available at an optimal cost.

Since the expense of inspection is increasing while the design rules of semiconductor devices are shrinking, it is becoming more critical to improve the device yield by distinguishing killer defect types in the early process stage for semiconductor manufacturers. In addition, more defect types have been discovered that impact device yield while new process steps have been created. Thus, the embodiments described herein can provide a new approach to identify defect types, and the methodology is flexible enough to apply to both existing and new wafer processes.

One potential application of the embodiments described herein is for improving defect classification efficiency for early detection of correctable process root causes to increase yield. Such applications may be useful for wafer suppliers. For example, wafer suppliers may use the embodiments to detect LLPD on PW, ESF on EPI wafers, and voids on SOI. IC device manufacturers may also use the embodiments described herein to detect oxide scratches on wafers caused by a chemical-mechanical polishing (CMP) process. Another potential application of the embodiments described herein is for screening and classifying yield killer defects to ensure better wafer quality. For example, the embodiments may be used for IC IQC to detect defects such as LLPD on PW, ESF on EPI wafers, and voids on SOI. An additional potential application of the embodiments described herein is for providing a flexible methodology to identify the maximum number of types of defects for existing and new processes. Such applications may be used by wafer suppliers and IC device manufacturers and for IC IQC.

In general, the optical architecture design for SPx unpatterned wafer defect inspection systems may be configured as described above. For example, as shown in FIG. 1, the optical architecture is generally configured for DF illumination using a light source such as a laser directed to wafer 14 as oblique incidence illumination 10 and normal incidence illumination 18. The channel collectors include wide channel collector 36 (and 38) configured to collect light 76 scattered from the wafer at relatively wide scattering angles and narrow channel collector 28 (and 30) configured to collect light 80 scattered from the wafer at relatively narrow angles. Light 82 reflected from the wafer due to normal incidence illumination may be collected by the narrow collector or blocked by the detection subsystem. Light 83 reflected from the wafer due to oblique incidence illumination may or may not be collected and detected. The optical architecture may be further configured as described herein. Such an optical subsystem may be used to detect particles and surface defects. In addition, a system in which such optical architecture is included may be further configured as described herein. For example, the system may include stage 20 that is configured to rotate wafer 14 in direction 84 such that the oblique incidence illumination and the normal incidence illumination scan over the wafer.

Figure 5:
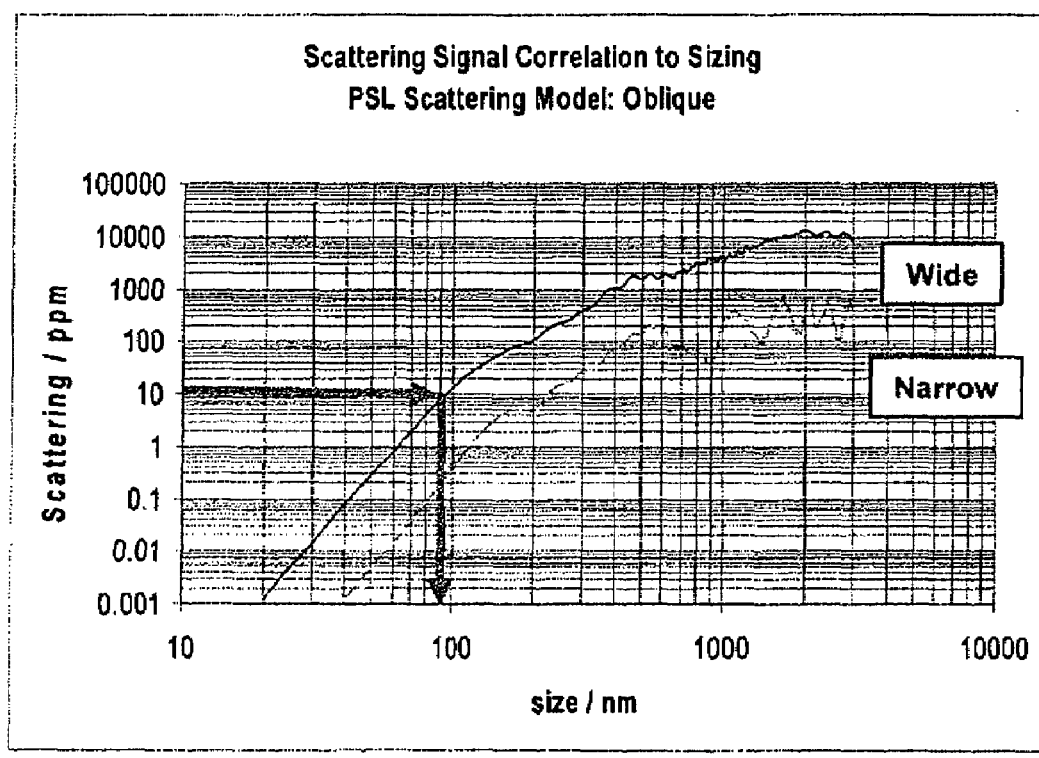
FIG. 5 is a plot illustrating a correlation of scattering signal intensity to defect sizing for one embodiment of a set of different combinations of illumination and collection channels of an inspection system.

The SPx systems are based on light scattering principles. The scattering intensity detected by the systems correlates to defect size, as shown in FIG. 5. In particular, as shown in FIG. 5, the scattering signal correlation to sizing may be determined using a polystyrene latex (PSL) sphere scattering model for oblique illumination. In FIG. 5, the scattering signal (in ppm) is plotted as a function of size (in nm) for oblique illumination with wide angle collection (wide) and narrow angle collection (narrow). As shown in FIG. 5, a particle will produce different scattering signals in different scattering angles. In addition, particles having different sizes produce different scattering signals in different scattering angles that can be correlated to each other.

Figure 6:
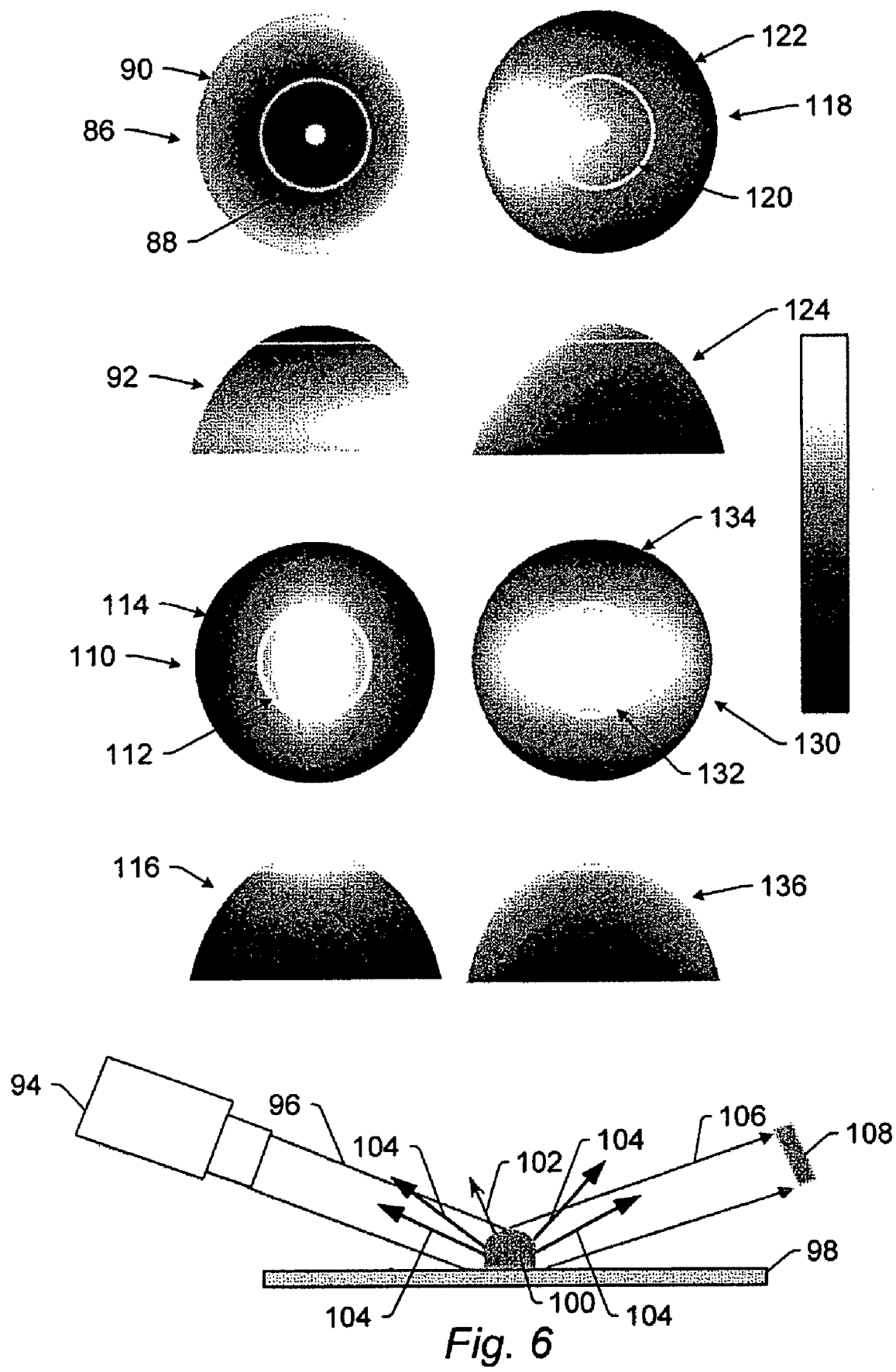
FIG. 6 is a schematic diagram illustrating examples of scattering patterns for different defect types illuminated by different illumination channels of an embodiment of an inspection system described herein and a side view of a portion of one embodiment of the inspection system.

The scattering pattern may also depend on one or more attributes of the defects such as materials, shapes, and sizes of the defects, one or more attributes of the surface of the substrate such as materials and roughness, and one or more attributes of the optical subsystem such as light polarization and incidence angle. Examples of such variations in the scattering pattern are illustrated in FIG. 6. In particular, scattering pattern 86 shows a top view of a scattering pattern for a particle defect type having a size of 70 nm illuminated at an oblique incidence angle. A narrow channel of the inspection system described herein would collect portion 88 of the scattering pattern while a wide channel of the inspection system would collect portion 90 of the scattering pattern outside of the narrow channel. Scattering pattern 92 shows a side view of scattering pattern 86.

A portion of an embodiment of an inspection system and a particle defect type that would produce such a scattering pattern is also illustrated in FIG. 6. In particular, as shown in FIG. 6, the inspection system includes light source 94, which may include a laser light source. The light source may direct incident beam 96 to wafer 98 at an oblique angle of incidence. Particle 100 on the wafer will scatter light 102 that is collected and detected by a narrow channel (not shown in FIG. 6) of the inspection system and light 104 that is collected and detected by a wide channel (not shown in FIG. 6) of the inspection system. Light 106 specularly reflected from the particle may be collected by beam position system (BPS) optics 108, which may include any suitable optics known in the art. As shown in FIG. 6, particle 100 scatters less light 102 to the narrow channel of the inspection system than to the wide channel of the inspection system thereby producing the relatively low intensity scattering pattern in portion 88 of scattering pattern 86 shown in FIG. 6 while the particle scatters more light 104 to the wide channel of the inspection system thereby producing the relatively high intensity scattering pattern in portion 90 of scattering pattern 86 shown in FIG. 6.

In contrast, scattering pattern 110 shows a top view of a scattering pattern for a particle defect type having a size of 70 nm illuminated at a normal incidence angle. A narrow channel of the inspection system described herein would collect portion 112 of the scattering pattern while a wide channel of the inspection system would collect portion 114 of the scattering pattern outside of the narrow channel. Scattering pattern 116 shows a side view of scattering pattern 110. As shown in scattering pattern 110, when the particle is illuminated with normal incidence illumination, the high intensity portion of the scattering pattern is portion 112 in the narrow channel while the lower intensity portion of the scattering pattern is portion 114 outside of the narrow channel. In this manner, when the particle is illuminated with normal incidence illumination, the scattering pattern is essentially reversed from that which would be seen when illuminating the particle with oblique incidence illumination.

Scattering pattern 118 shows a top view of a scattering pattern for a COP defect type having a size of 70 nm illuminated at an oblique incidence angle. A narrow channel of the inspection system described herein would collect portion 120 of the scattering pattern while a wide channel of the inspection system would collect portion 122 of the scattering pattern outside of the narrow channel. Scattering pattern 124 shows a side view of scattering pattern 118. In contrast with scattering pattern 118, scattering pattern 130 shows a top view of a scattering pattern for a COP defect type having a size of 70 nm illuminated at a normal incidence angle. A narrow channel of the inspection system described herein would collect portion 132 of the scattering pattern while a wide channel of the inspection system would collect portion 134 of the scattering pattern outside of the narrow channel. Scattering pattern 136 shows a side view of scattering pattern 130.

As shown in FIG. 6, the scattering patterns produced by a COP defect type are substantially different when the angle of incidence at which the COP defect type is illuminated is changed. In addition, the scattering patterns for the particle and COP defect types are substantially different when illuminated with both oblique and normal incidence illumination. Therefore, the differences between the scattering patterns for these defect types may be used to differentiate between and identify the defect types.

A light scattering model can be used to predict an optimal combination of angle of incidence, collectors and channels for DOI classification. For example, as shown in FIG. 7, different defect types exhibit different scattering patterns. In particular, FIG. 7 illustrates scattering patterns for different defect types illuminated by different illumination channels of the inspection system described herein. Scattering pattern 166 is for a particle defect type having a size of 30 nm illuminated with oblique incidence illumination, and scattering pattern 168 is for the particle defect type having a size of 30 nm illuminated with normal incidence illumination. Scattering pattern 138 is for a particle defect type having a size of 70 nm illuminated with oblique incidence illumination, and scattering pattern 140 is for the particle defect type having a size of 70 nm illuminated with normal incidence illumination. Scattering pattern 142 is for a particle defect type having a size of 200 nm illuminated with oblique incidence illumination, and scattering pattern 144 is for the particle defect type having a size of 200 nm illuminated with normal incidence illumination. Scattering pattern 146 is for a COP defect type having a size of 70 nm illuminated with oblique incidence illumination, and scattering pattern 148 is for the COP defect type having a size of 70 nm illuminated with normal incidence illumination. The light scattering model used to generate the light scattering patterns shown in FIG. 7 is a finite element model.

One DOI for PW includes COP type defects. As shown in FIG. 8, the scattering patterns for different defect types illuminated with the same illumination channel are substantially different from each other. In this manner, different types of DOI scatter in discrete patterns that may be used for separating the DOI from particles. For example, scattering pattern 138 for a particle type defect having a size of 70 nm illuminated at an oblique incidence angle produces more scattering in the wide channel than in the normal channel while scattering pattern 146 for a COP defect type having a size of 70 nm illuminated at the same oblique incidence angle produces more scattering in the narrow channel.

Therefore, for a PW COP defect type, as shown in FIG. 2, a combination of an oblique incidence illumination channel and a wide angle collection channel (oblique wide 46) and a combination of the oblique incidence illumination channel and a narrow angle collection channel (oblique narrow 48) can be used to inspect PWs, and output acquired by the oblique wide combination and the oblique narrow combination can be used to determine if the defects are COP defects or particle defects. For example, the scattering in the wide channel and narrow channel can be compared (as shown by arrow 178) to determine if the defects are COP defects or particle defects. In this manner, the method may include identifying COP and particle defect types of defects detected on PWs based on output acquired by a set of different combinations that includes oblique wide 46 and oblique narrow 48.

COP type defects on PWs can be differentiated from particle and scratch type defects on the PWs with relatively high accuracy and relatively high purity (e.g., accuracy and purity greater than about 90%) by comparing scattering patterns generated by oblique incidence illumination and narrow and wide channel collection, as shown in FIG. 9. In particular, as shown in FIG. 9, scanning electron microscope (SEM) review was used to determine that the accuracy and purity of identifying COP defect types separately from particle and scratch defect types on PWs performed in a run time defect classification (RTDC) mode using output acquired by the oblique wide combination and the oblique narrow combination are substantially high.

Figure 10:
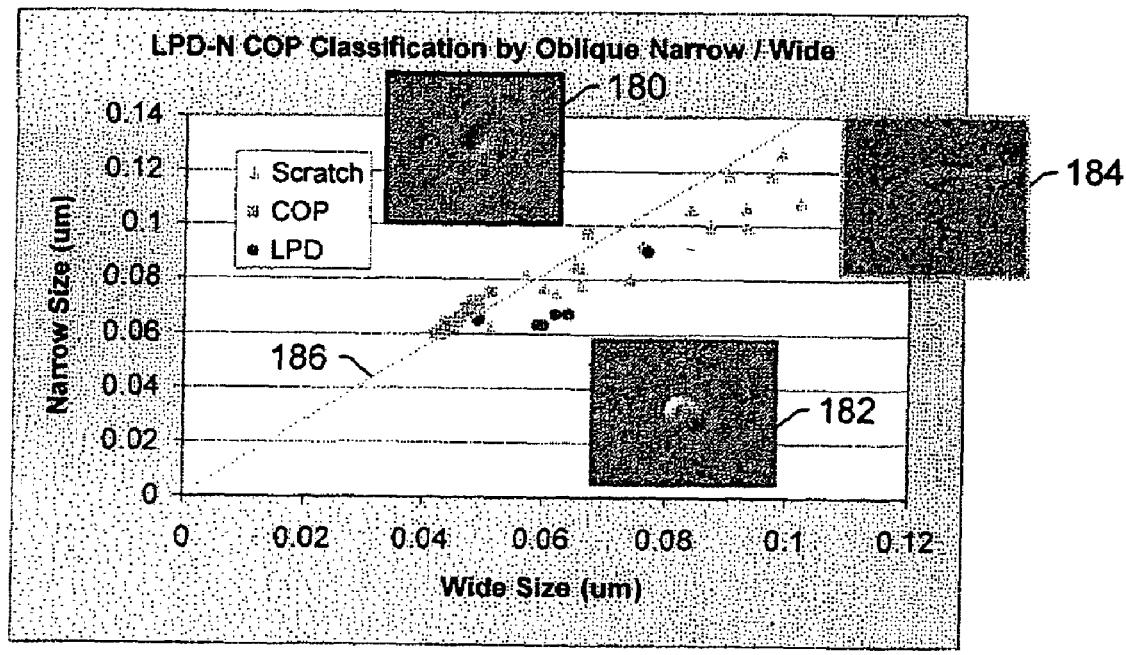
FIG. 10 is a plot illustrating different reported sizes for defects identified as COP, LPD, and scratch defect types separately determined using output acquired by the different combinations included in a set shown in FIG. 2.

In addition, the differences in the scattering produced by different defect types may affect the defect size that is determined by the inspection system for the different defect types. For instance, as shown in FIG. 10, sizes for different types of defects were determined based on the scattering from the different types of defects detected using oblique incidence illumination and narrow channel collection, and the sizes were determined based on the scattering from the different types of defects detected using oblique incidence illumination and wide channel collection. In particular, sizes of defects identified as scratch defect types, COP defect types, and LPD defect types reported by the oblique narrow combination were plotted as a function of sizes of the same defects reported by the oblique wide combination. Images of examples of such defect types are also shown in FIG. 10. In particular, image 180 is an image of a defect identified as a COP defect type, image 182 is an image of a defect identified as an LPD defect type, and image 184 is an image of a defect identified as a scratch defect type.

In general, when plotted as described above, the sizes of COP defect types on PWs determined as described above are clustered together separately from the sizes of the scratch and LPD defect types determined as described above. In addition, the sizes determined for the COP defect types can be generally separated from the sizes determined for the scratch and LPD defect types by line 186 shown in FIG. 10. Therefore, sizes determined as described above for defects that are of an unknown type may be plotted in a graph with this line (which may be a linear slope, vertical or horizontal line, as well as a polynomial fitting curve), and the position of the sizes with respect to this line may be used to determine the defect type.

Figure 11:
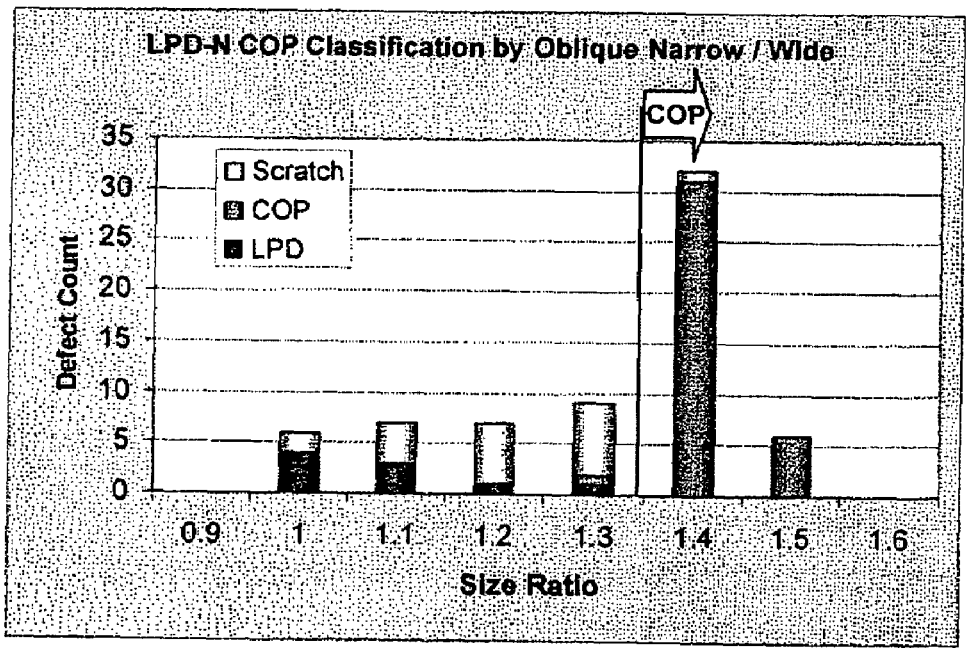
FIG. 11 is a plot illustrating ratios of the different reported sizes shown in FIG. 10.

In addition, the sizes determined for each defect as described above can be used to determine a defect size ratio for each defect, and the relationship described above in the size differences for different defect types can be expressed as a defect size ratio threshold that can be compared to the defect size ratio determined for defects of unknown types to determine the defect type. In this manner, a ratio of the defect sizes reported by different combinations included in a set may be determined and compared to a threshold to identify the defect types. For instance, a defect having a ratio of a size determined using output acquired by a combination of narrow channel collection and oblique incidence illumination to a size determined using output acquired by a combination of wide channel collection and oblique incidence illumination that is equal to or greater than a threshold of about 1.4 may be determined to be a COP defect, as shown in FIG. 11.

DOI for PWs include LLPD. In particular, device killing LLPD that may be introduced during wafer processing include crystal pulling defects (LLPD air pockets) and polishing process defects (LLPD polishing defects). Images of examples of such defects are illustrated in FIG. 12. In particular, image 188 is an image of one example of an LLPD air pocket defect type, and image 190 is an image of one example of an LLPD polishing defect type. Such DOI for PW can be identified using both DF and BF DIC. For instance, LLPD air pockets are generally large in size which may have a width of about 10 µm to about 100 µm and a depth of about 10 µm. BF DIC can be used to detect relatively large and/or relatively flat defects. Therefore, BF DIC may be advantageously used to classify LLPD. For example, using FIG. 2 to illustrate, LLPD air pocket defect types can be identified by using output acquired by BF DIC for a defect and output acquired for the defect by oblique incidence illumination with wide collection (as shown by arrow 192) or narrow collection (as shown by arrow 194) or by normal incidence illumination with wide collection (as shown by arrow 196) or narrow collection (as shown by arrow 198). In this manner, LLPD air pockets can be identified by comparing the output acquired by BF DIC 54 for a defect to the output acquired for the defect by a combination of oblique wide 46, oblique narrow 48, normal wide 50, or normal narrow 52.

In one such example, FIG. 13 illustrates a set of wafer maps showing defects detected by both oblique incidence DF and normal incidence DF, defects detected by BF DIC, and defects detected by both DF and BF DIC. As shown in FIG. 13, oblique and normal incidence illumination DF inspection may result in detection of a first set of defects as illustrated in wafer map 200 showing 1509 defects. BF DIC inspection of the same wafer may result in detection of a second set of defects as illustrated in wafer map 202 showing 40 defects. Defects that are included in both the first and second sets of defects at substantially the same location in the wafer maps may be identified as LLPD, which are illustrated in wafer map 204 in FIG. 13 showing 13 defects. These 13 defects are, therefore, defects that are common to the DF inspection described above and BF DIC.

Relatively high accuracy and relatively high purity defect classification can be achieved using DF and BF DIC as described above. For example, as shown in FIG. 14, LLPD defects can be differentiated from LPD defects with relatively high accuracy and relatively high purity (e.g., accuracy and purity greater than about 90%) by comparing output acquired using DF and output acquired using BF DIC. In particular, as shown in FIG. 14, SEM review was used to determine that the accuracy and purity of identifying LLPD defect types separately from LPD defect types in an RTDC mode using output acquired by DF normal incidence illumination and BF DIC are substantially high.

Figure 15:
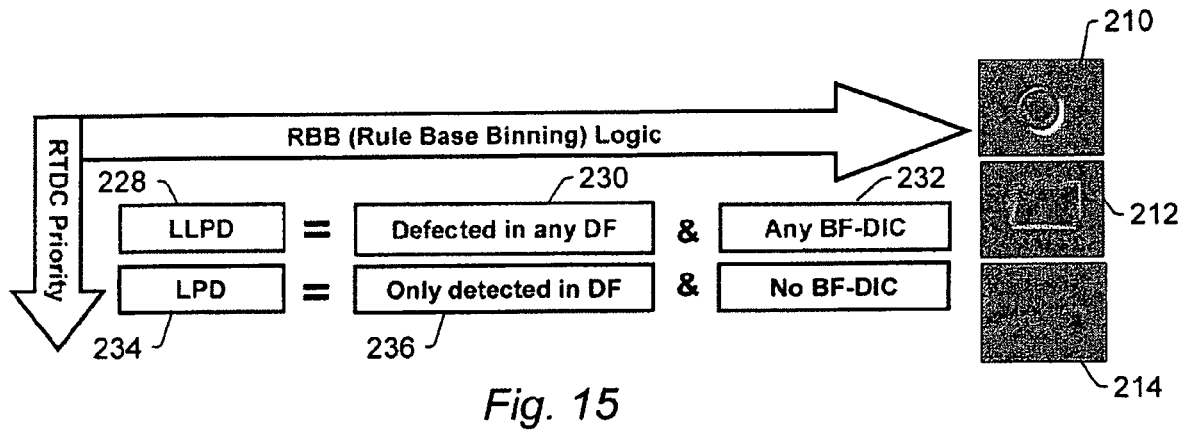
FIG. 15 is a schematic diagram that includes images of examples of different defect types and examples of rules that may be used to classify such defect types using rule based binning (RBB)

The scattering characteristics described above can be used to setup rule based binning (RBB) logic or one or more algorithms. Images of examples of different defect types that may be classified by examples of RBB rules are illustrated in FIG. 15. In general, LLPD defect types may include air pocket, wafering and polishing defect types which result from different manufacturing sources. For example, as shown in FIG. 15, image 210 is an image of one example of an air pocket defect type, image 212 is an image of one example of a wafering defect type, and image 214 is an image of one example of a polishing defect type. One example of a RBB rule that may be used to classify defects in an RBB method is that LLPD 228 may be assigned to a defect if the defect is detected in DF 230 and for any BF DIC 232 output acquired for the defect. Another example of a rule that may be used to classify defects in an RBB method is that LPD defect 234 may be assigned to a defect that is only detected in DF (e.g., is detected in DF but not by BF DIC) (only detected in DF 236). In addition, FIG. 15 shows that the RTDC priority for such defect types may be, from highest to lowest priority: e.g., LLPD type defects and LPD type defects. The priority of the defects may be determined in any suitable manner (e.g., the probability that a defect type will kill a device).

DOI for EPI wafers include SF. The embodiments described herein may be used to identify SF type defects as such by using scattering detected by the combination of oblique incidence illumination and wide channel collection vs. the combination of normal incidence illumination and narrow channel collection. For example, using FIG. 2 to illustrate, identifying SF type defects on EPI wafers may be performed using output acquired by oblique wide 46 and output acquired by normal narrow 52. In this manner, identifying SF type defects on EPI wafers may be performed based on output acquired by a set of the oblique wide combination and the normal narrow combination. Classifying SF type defects on EPI wafers may include comparing scattering detected using the combination of oblique incidence illumination and wide channel collection compared to scattering detected using the combination of normal incidence illumination and narrow channel collection (as shown by arrow 238). In this manner, output produced by scanning a wafer with normal incidence illumination and oblique incidence illumination may be used to identify SF type defects on EPI wafers. For example, all key DOI for EPI wafers may be detected by the combination of oblique incidence illumination and wide channel collection and the combination of normal incidence illumination and narrow channel collection but not by the combination of oblique incidence illumination and narrow channel collection and the combination of normal incidence illumination and wide channel collection. In this manner, the best detection of defects on EPI wafers may be achieved by using the combination of oblique incidence illumination and wide channel collection and the combination of normal incidence illumination and narrow channel collection. For example, normal incidence illumination, narrow channel collection defect detection and oblique incidence illumination, wide channel collection defect detection may provide about 25% better detection capability for DOI than other defect detection configurations described herein.

Figure 16:
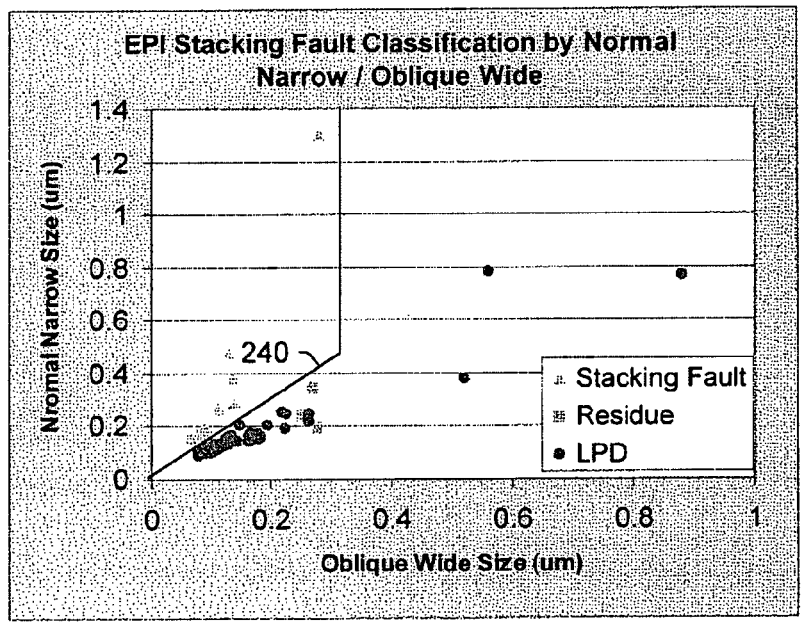
FIG. 16 is a plot illustrating different reported sizes for defects identified as SF, residue, and LPD defect types separately determined using the different combinations included in a set shown in FIG. 2.

The differences in the scattering produced by different defect types may affect the defect size that is determined by the inspection system described herein for the different defects. For instance, as shown in FIG. 16, sizes for different types of defects were determined based on the scattering intensity from the different types of defects detected using normal incidence illumination and narrow collection channel, and the sizes were also determined based on the scattering intensity from the different types of defects detected using oblique incidence illumination and wide channel collection. In particular, sizes of defects identified as SF defect types, residue defect types, and LPD defect types reported by the normal narrow combination were plotted as a function of sizes of these defects reported by the oblique wide combination.

In general, when plotted as described above, the sizes of SF defect types determined as described above are clustered together separately from the sizes of the residue and LPD defect types determined as described above. The sizes of other key EPI DOI such as hillocks and dislocations determined in the manner described above may also show clear separation from other defects detected on EPI wafers. In addition, the sizes determined for the SF defect types can be generally separated from the sizes determined for the residue and LPD defect types by line 240 shown in FIG. 16. The vertical portion of line 240 corresponds to a threshold for oblique wide size less than 0.3. Therefore, sizes determined in the manner described above for defects that are of an unknown type may be plotted in a graph with this line, and the position of the sizes with respect to this line may be used to identify the defect type. As such, the relatively good separation in defect sizing determined using output acquired by the combination of normal incidence illumination and narrow channel collection and using output acquired by the combination of oblique incidence illumination and wide channel collection can be used to distinguish EPI DOI from non-EPI DOI.

Figures 17, 18:
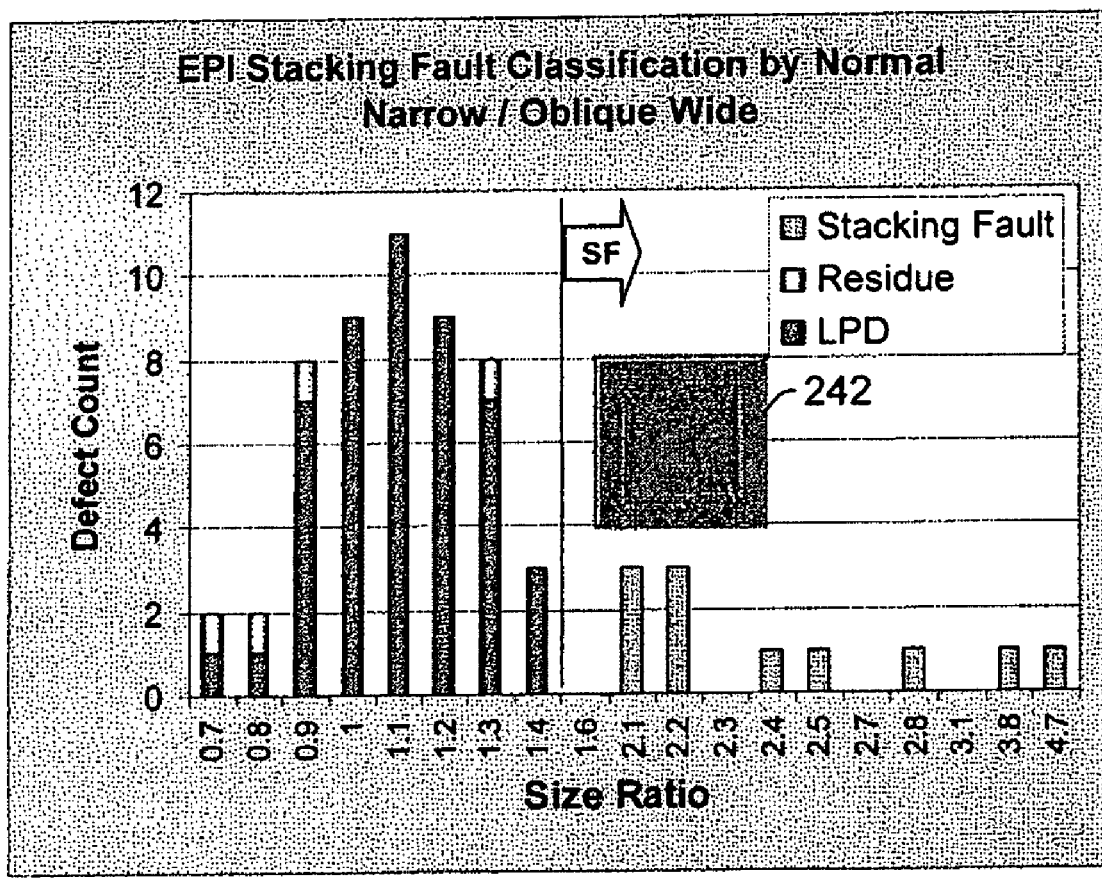
FIG. 17 is a plot illustrating ratios of the different reported sizes shown in FIG. 16.
FIG. 18 is a table illustrating classification accuracy and purity results for identifying SF defect types separately from LPD and residue defect types using output acquired by a set of the different combinations shown in FIG. 2.

In addition, the sizes determined as described above for each defect can be expressed as a defect size ratio for each defect, and the relationship described above in the size differences for different defect types can be expressed as a defect size relationship (e.g., linear or polynomial fitting curve) threshold that can be compared to defect size ratios determined for defects of unknown types to identify the defect types. In this manner, a ratio of the defect sizes reported by different combinations included in a set may be determined and compared to a threshold to identify the defect types. For instance, a defect for which, as shown in FIG. 17, a ratio of a size determined using output acquired by a combination of narrow channel collection and normal incidence illumination to a size determined using output acquired by a combination of wide channel collection and oblique incidence illumination is equal to or greater than a threshold of about 1.5 and, as shown in FIG. 16, for which a size determined using output acquired by a combination of wide channel collection and oblique incidence illumination is equal to or less than about 0.3 μm, may be determined to be a SF defect. Image 242 shown in FIG. 17 is an image of one example of a SF defect. Therefore, SF defects can be separated from other types of defects detected on EPI wafers by a combination of a DF, narrow collection, normal illumination size to a DF, wide collection, oblique illumination size ratio that is equal to or greater than about 1.5, and a DF, wide collection, oblique illumination size that is equal to or less than about 0.3 μm.

SF classification performed as described above using output acquired by the oblique wide combination and the normal narrow combination can achieve relatively high classification accuracy and relatively high purity, as shown in FIG. 18. For example, as shown in FIG. 18, SF defects can be differentiated from LPD and residue defects with relatively high accuracy and relatively high purity (e.g., accuracy and purity of about 100%) by comparing output acquired using an oblique wide combination and output acquired using a normal narrow combination. In particular, as shown in FIG. 18, SEM review was used to determine that the accuracy and purity of identifying SF defect types separately from LPD and residue defect types in an RTDC mode using output acquired by the oblique wide combination and the normal narrow combination are substantially high.

Classification of defects detected on EPI wafers may be optimized in a number of manners. For example, in one embodiment, the method includes subtracting defects commonly detected by the different combinations included in the set from the defects detected on the wafer prior to identifying the defect types. In one such example, defects detected on EPI wafers by the combination of oblique incidence illumination and wide channel collection may include EPI DOI such as hillocks and dislocations and also non-DOI for EPI wafers such as LPD. In addition, defects detected on EPI wafers by the combination of normal incidence illumination and narrow channel collection may include EPI DOI such as those described above as well as LPD. Therefore, the defect population for which classification is performed may include non-EPI DOI, which may adversely affect the purity and accuracy of the defect classification results. However, non-EPI DOI may be removed from the defect population prior to defect classification by subtracting defects detected using output acquired by the combination of normal incidence illumination and wide channel collection and using output acquired by the combination of oblique incidence illumination and narrow channel collection. Subtracting defects common to a defect population detected by normal incidence illumination and wide channel collection and a defect population detected by oblique incidence illumination and normal channel collection from the defect population for the wafer prior to defect classification may improve classification results for certain EPI DOI. Removing such non-EPI DOI prior to defect classification may be particularly advantageous for improving the purity of the defect classification results. In some instances, increasing the purity of the defect classification results may result in a lower accuracy of the defect classification results. However, the accuracy of the defect classification results can be maintained and/or increased by optimizing one or more parameters of the inspection process.

DOI for SOI wafers include voids and stains. Classifying void and particle defect types may include comparing the scattering in the wide channel using oblique incidence illumination to the scattering in the narrow channel using normal incidence illumination (as shown by arrow 238 in FIG. 2). In this manner, dual incidence illumination (both normal incidence illumination and oblique incidence illumination) may be used to ensure SOI quality.

Figures 19, 20:
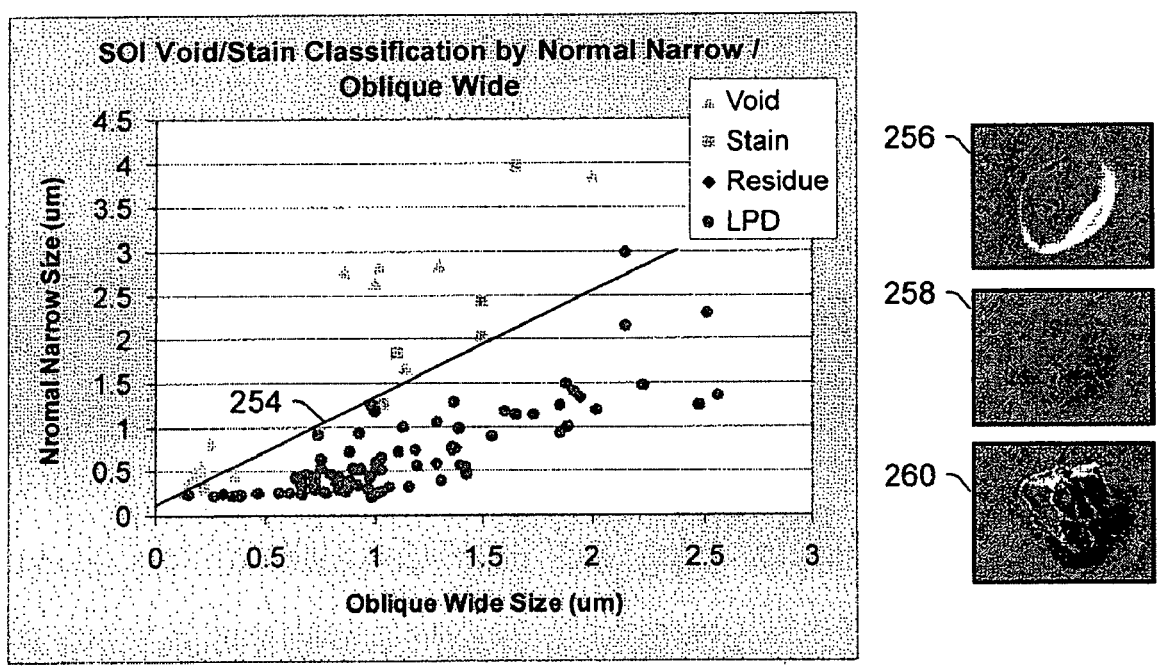
FIG. 19 is a table illustrating classification accuracy and purity results for identifying void and stain defect types separately from LPD and residue defect types using output acquired by a set of the different combinations shown in FIG. 2.
FIG. 20 is a plot illustrating different reported sizes for defects identified as void, stain, residue, and LPD defect types separately determined using output acquired by the different combinations included in a set shown in FIG. 2 and images of examples of void, stain, and LPD defect types.

Classification performed as described above using output acquired by the oblique wide combination and by the normal narrow combination can achieve relatively high classification accuracy and relatively high purity, as shown in FIG. 19. For example, as shown in FIG. 19, void and stain defects can be differentiated from LPD and residue defects with relatively high accuracy and relatively high purity (e.g., accuracy and purity of greater than about 89%) by comparing output acquired using an oblique wide combination to output acquired using a normal narrow combination. In particular, as shown in FIG. 19, SEM review was used to determine that the accuracy and purity of identifying void and stain defect types separately from LPD and residue defect types performed in an RTDC mode using output acquired by the oblique wide combination and the normal narrow combination are substantially high.

The differences in the scattering produced by different defect types may affect the defect size that is determined by the embodiments described herein for the different defect types. For instance, as shown in FIG. 20, sizes for different types of defects were determined based on the scattering from the different types of defects detected using the combination of normal incidence illumination and narrow channel collection, and the sizes were determined based on the scattering from the different types of defects detected using the combination of oblique incidence illumination and wide channel collection. In particular, sizes of defects identified as void, stain, residue, and LPD defect types reported by the normal narrow combination were plotted as a function of sizes of these defects reported by the oblique wide combination. Image 256 shown in FIG. 20 is an image of one example of a void defect. Image 258 shown in FIG. 20 is an image of one example of a stain defect, and image 260 shown in FIG. 20 is an image of one example of an LPD defect.

In general, when plotted as described above, the sizes of defects identified as void and stain defect types are clustered together separately from the sizes of defects identified as residue and LPD defect types. In addition, the sizes determined for defects identified as the void and stain defect types can be generally separated from the sizes determined for defects identified as the residue and LPD defect types by line 254 shown in FIG. 20. Therefore, sizes determined in the manner described above for defects that are of an unknown type may be plotted in a graph with this line, and the position of the sizes with respect to this line may be used to determine the defect type.

Figures 21, 22:
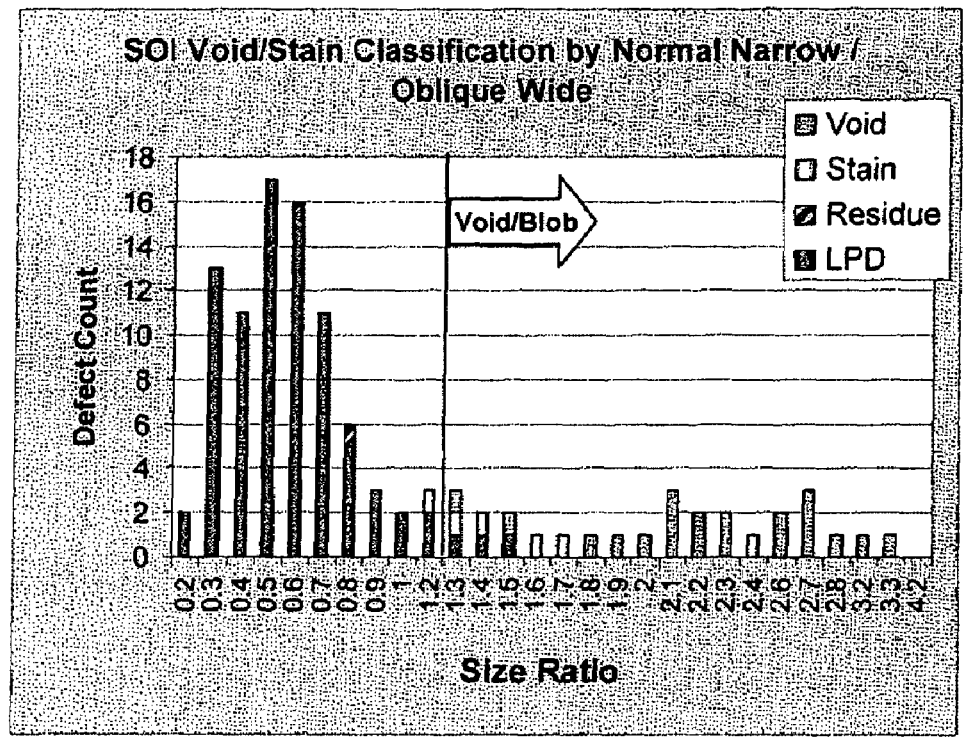
FIG. 21 is a plot illustrating ratios of the different reported sizes shown in FIG. 20.
FIG. 22 is a table illustrating different combinations of illumination and collection channels of one embodiment of an inspection system that may be included in a set, output acquired by which may be used in embodiments described herein for identifying different defect types on different wafer types.

In addition, the sizes determined as described above for each defect can be expressed as a defect size ratio for each defect, and the relationship described above in the size differences for different defect types can be expressed as a defect size ratio relationship (e.g., linear or polynomial fitting curve) threshold. This threshold can be compared to defect size ratios determined for defects of unknown type to identify the defect types of the defects. In this manner, a ratio of the defect sizes reported by different combinations included in a set may be determined and compared to a threshold to identify the defect types. For instance, a defect for which a ratio of a size determined based on scattering detected by a combination of narrow channel collection and normal incidence illumination to a size determined based on scattering detected by a combination of wide channel collection and oblique incidence illumination is equal to or greater than a threshold of about 1.3 may be determined to be a void or stain defect, as shown in FIG. 21. Therefore, void and stain defects can be separated from other types of defects detected on SOI wafers by a DF, narrow collection, normal incidence illumination size to a DF, wide collection, oblique incidence illumination size ratio that is equal to or greater than about 1.3.

The cross-channel results described above demonstrate effective classification of DOI for PW, EPI wafers, and SOI wafers. For the 45 nm technology node, other than the usual demands for increases in defect sensitivity, capturing all DOI also becomes critical. In addition, a normal incidence illumination inspection scan and BF may be advantageously used for detection and classification of DOI on PW, EPI wafers, and SOI wafers. However, an oblique incidence illumination inspection scan in of itself may not provide sufficient information to classify DOI. IC IQC preferably sorts out DOI before the DOI impact device yield. Therefore, wafer manufacturers need early detection and classification of DOI to determine the root cause of defects in wafer processing. As described herein, the embodiments may utilize all available combinations of channels for classification of defects. Such channels may include oblique and normal incidence illumination. In addition, the embodiments described herein may utilize a cross-channel size comparison. The embodiments described herein may also include a BF application for certain DOI as described further herein. Furthermore, the embodiments described herein may advantageously use a cross-channel size comparison to classify DOI with relatively high accuracy and relatively high purity (e.g., an accuracy of greater than about 80% and a purity of greater than about 80%). Such DOI may include COP and LLPD for PW, SF for EPI wafers, and voids and/or stains for SOI wafers.

FIG. 22 illustrates combinations of channels that may be used to classify some of the DOI in the embodiments described herein. In particular, a set of the different combinations that includes oblique wide and oblique narrow may be used to identify COP defect types on PW. A set of the different combinations that includes oblique wide, oblique narrow, normal wide, normal narrow, and BF DIC may be used to identify LLPD defect types on PW. A set of the different combinations that includes oblique wide and normal narrow may be used to identify SF defect types on EPI wafers. In addition, a set of the different combinations that includes oblique wide and normal narrow may be used to identify void and stain defect types on SOI wafers.

In addition, classification of more DOI may be performed by scanning the wafer during inspection using normal incidence illumination or by using output generated by such scanning to classify the DOI. Therefore, the different channels may include not only different collection channels, but different collection channels and/or different incidence illumination.

As described above, scattering characteristics can be used to setup RBB logic or one or more algorithms. In one embodiment, identifying the defect types includes determining a function of different reported sizes for the defects separately determined from the output acquired by the different combinations included in the set and using the function as an attribute for RBB. For example, DF physical channel size ratios can be used as attributes in a RBB classifier. DF physical channel size ratios can be used as attributes for RBB to enable the description of the detection size from any two physical channels as a ratio to provide another dimension that can be used for binning LPDs. With dual scan capability, output may be generated by up to four physical combinations of channels in one inspection. These channels may be: oblique incidence illumination, wide channel collection (oblique wide); oblique incidence illumination, narrow channel collection (oblique narrow); normal incidence illumination, wide channel collection (normal wide); and normal incidence illumination, narrow channel collection (normal narrow). The possible ratio combinations may then be: oblique wide, oblique narrow; normal wide, normal narrow; oblique wide, normal wide; oblique wide, normal narrow; oblique narrow, normal wide; and oblique narrow, normal narrow, as shown in FIG. 2.

The ratios listed above may be used in combination with other defect attributes to assist in the binning of DOI detected by DF on various films and various wafer types. This binning may be performed using a RBB engine. This capability in particular will allow the binning of DOI on wafer types such as SOI wafers, EPI wafers, and PW. Furthermore, in addition to ratios, the function of the different reported sizes for the defects that may be determined as described above and used as an attribute for RBB include vertical or horizontal line functions as well as polynomial curve functions to describe relationships between different sizing of the defects to identify a defect type.

The embodiments described herein may allow a user to select which DF physical channel output is combined and which rules are used for defect detection and/or classification. The user may be allowed to create a new defect type identifier that can be used by data processing to be associated with the RBB output. In an RTDC page of a recipe, if the user selects the RBB classifier, the RBB user interface (UI) shown in FIG. 23 may be shown, and the user can select, apart from just the size and location of a defect, the defect's size ratio between two physical channels as well as a defect size polynomial fitting relationship between two physical channels. The user may also be able to select a rough bin code with which the RBB output may be identified. The RBB output may include a KLARF file and defect wafer maps.

Figure 23:
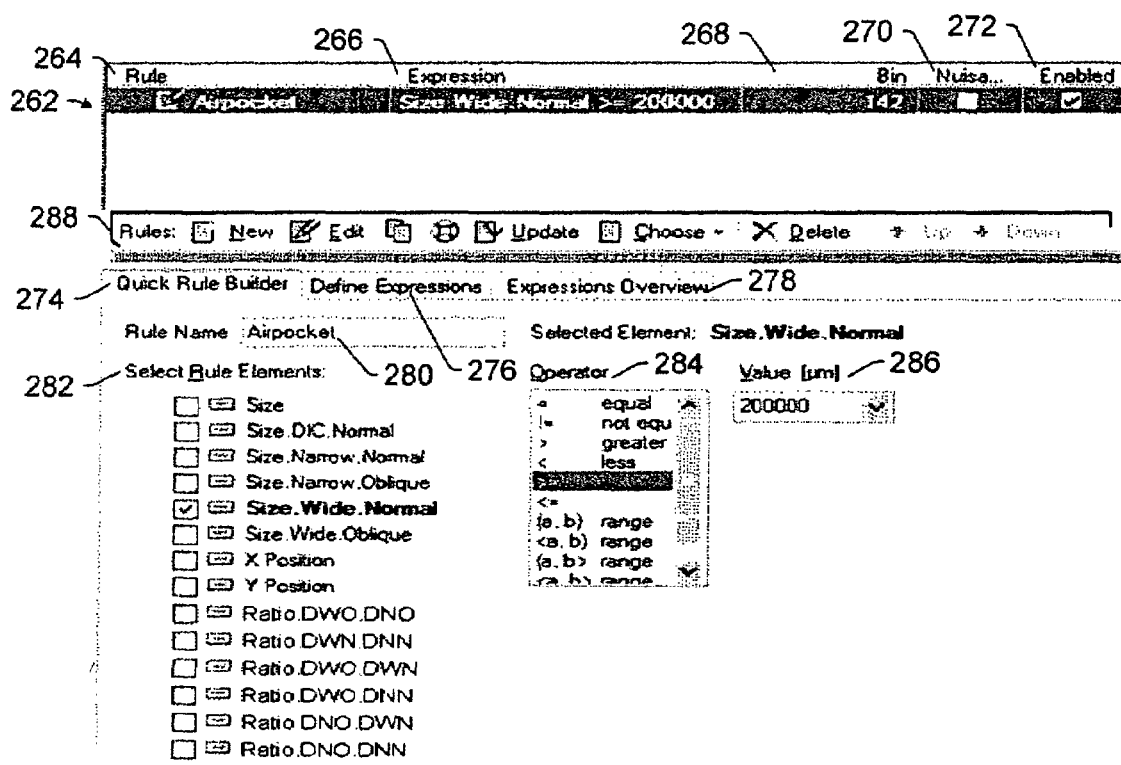
FIG. 23 is a screenshot of one embodiment of a user interface that can be used to set up a RBB method.

For example, as shown in FIG. 23, the UI may include list 262 showing rule names 264 (e.g., Airpocket), expressions 266 corresponding to the rules (e.g., Size.Wide.Normal>=200000), rough bin code 268 (e.g., 142), whether or not the defects binned by the rule are nuisance 270, and whether or not the rule is enabled 272. In addition, the UI may include tabs for creating rules. For example, the UI may include Quick Rule Builder tab 274, Define Expressions tab 276, and Expressions Overview tab 278. As shown in FIG. 23, selecting Quick Rule Builder tab 274 allows a user to create a rule by entering rule name in box 280, selecting rule elements 282 (e.g., by checking one or more of the boxes in the list of possible rule elements), selecting one or more operators from operator list 284 for each of the selected elements, and selecting a value from value drop down menu 286. In addition, as shown in FIG. 23, the UI may include a number of additional icons 288 that the user can click on to perform additional functions. The additional functions may include any suitable functions, and the additional icons may include any suitable icons.

Once the user sets the bin, applicable defect attributes, and results, these parameters may be saved as part of the recipe. When the scan runs, the embodiments described herein may generate summary items and show the new defects classified using the RBB rules on a multiple channels defect map.

The user may add new defect types along with the rough bin codes in a "configuration UI" and come to the recipe RTDC component and select the RBB classifier. After selecting the RBB classifier, a UI such as that shown in FIG. 23 may be displayed to the user. The user may be allowed to select any of Rule Elements that are available as part of the recipe setup. The user may set more than one rule per instance of the RBB classifier. The user can also add multiple instances of the RBB classifier in the RTDC page to setup more than one rule. The list of the DF physical channel size ratios that may be used as attributes, for all of the possible cases include: ratio oblique wide, oblique narrow; ratio normal wide, normal narrow; ratio oblique wide, normal wide; ratio oblique wide, normal narrow; ratio oblique narrow, normal wide; and ratio oblique narrow, normal narrow. The size relationship between multiple physical channels is not limited to the above ratio operator or linear function slope, e.g., vertical or horizontal functions as well as a polynomial curve function relationships may also be implemented.

Figure 24:
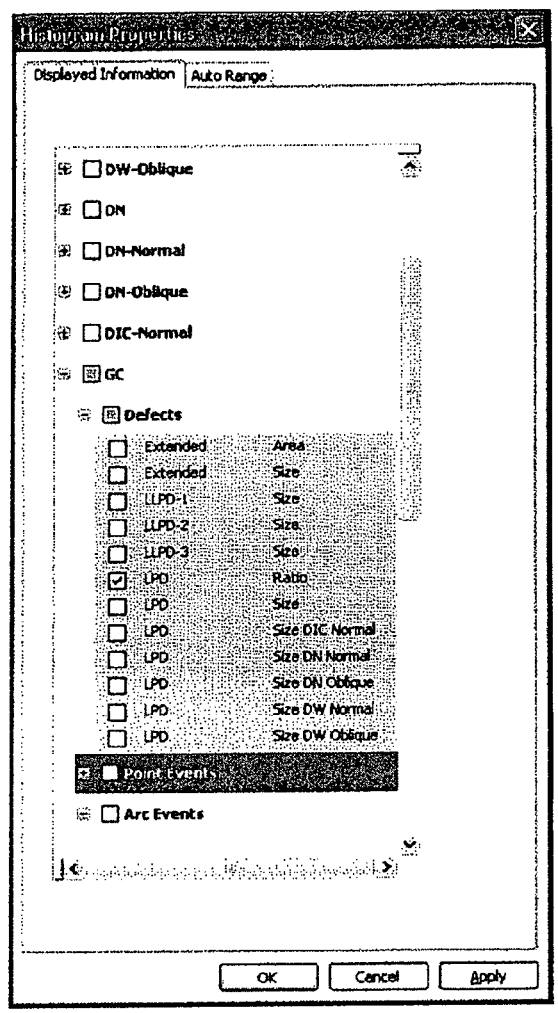
FIG. 24 is a screenshot of one embodiment of a user interface that can be used to select the properties of a histogram in which results of the RBB method are to be displayed.
Figure 25:
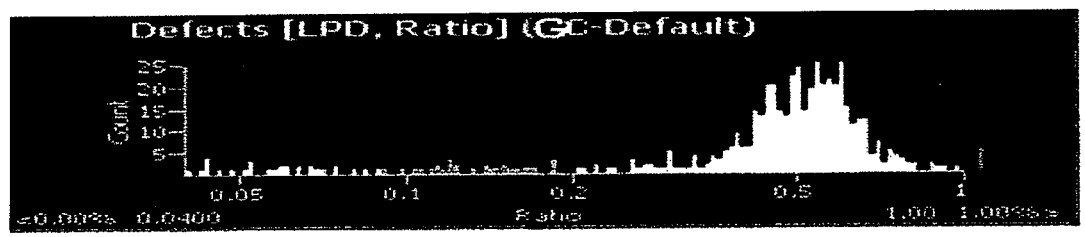
FIG. 25 is a defect histogram of one example of results of the RBB method.

Output of the RBB processing may include a summary showing the details of the new defect type(s) and a map that can display the defect type(s). In addition, a KLARF may include the defect data with the appropriate defect rough bin code as selected by the user in the classifier. The user may be able to go to the display properties of the multiple defect channels, as shown in FIG. 24, and select the ratio of the channels in the RBB classifier to be displayed in the channel's defect histogram. One example of such a defect histogram is shown in FIG. 25. Such a defect histogram may be generated based on selections that a user may make in the user interface shown in FIG. 24. For example, as shown in FIG. 24, in the Displayed Information tab of the Histogram Properties window, selecting GC, Defects, and LPD Ratio produces the histogram shown in FIG. 25. Other selections in the Displayed Information tab can be used to generate other histograms.

The composite channel may be implemented for all inspections, both with single illumination with or without BF enabled, and dual illumination with or without BF enabled. The composite channel may be used to pool defect attributes based on RBB rules.

The embodiments described herein may also include storing results of one or more methods and/or one or more computer-implemented methods described herein in a storage medium. In addition, the embodiments described herein may be configured to store results of one or more methods and/or one or more computer-implemented methods described herein in a storage medium. The results may include any of the results described herein such as identified or determined defect types or classifications. The results may be stored in any manner known in the art. In addition, the storage medium may include any suitable storage medium known in the art. After the results have been stored, the results can be accessed in the storage medium and used by any of the method or system embodiments described herein. Furthermore, the results may be stored "permanently," "semi-permanently," temporarily, or for some period of time. For example, the storage medium may be random access memory (RAM), and the results may not necessarily persist in the storage medium.

The methods described herein may include monitoring semiconductor fabrication processes using the results of the methods. The results that are used to monitor the semiconductor fabrication processes may include any of the results described herein or any combination of the results described herein. The methods described herein may also include altering one or more parameters of one or more semiconductor fabrication processes based on the results of any of the methods described herein. The parameter(s) of the semiconductor fabrication process(es) may be controlled using a feedback technique, a feedforward technique, an in situ technique, or some combination thereof. In this manner, the methods described herein and the results generated by the methods may be used for SPC applications.

Each of the embodiments described herein may also include any step(s) of any method(s) described in commonly assigned U.S. Pat. No. 6,891,611 to Vaez-Iravani et al., which is incorporated by reference as if fully set forth herein. In addition, each of the embodiments described herein may be further configured as described in this patent.

Further modifications and alternative embodiments of various aspects of the invention may be apparent to those skilled in the art in view of this description. For example, methods and systems for identifying defect types on a wafer are provided. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A computer-implemented method for identifying defect types on a wafer, comprising:

acquiring output of an inspection system for defects detected on a wafer, wherein the output is acquired by different combinations of illumination and collection channels of the inspection system; and identifying defect types of the defects based on the output acquired by a set of the different combinations by separately determining different reported sizes for the defects from the output acquired by the different combinations included in the set and identifying the defect types of the defects based on a function of the different reported sizes for the defects, wherein the set of the different combinations is selected based on the defect types to be identified on the wafer and a wafer type of the wafer such that a different set of the different combinations of the illumination and collection channels is used for identifying different defect types on different wafer types, and wherein the defect types of the defects comprise defect types other than particles and crystal-originated pits.

2. The method of claim 1, wherein the defect types of the defects further comprise one or more yield killing defect types.

3. The method of claim 1, wherein the set of the different combinations comprises all available combinations of the illumination and collection channels of the inspection system.

4. The method of claim 1, wherein the set of the different combinations comprises a subset of all available combinations of the illumination and collection channels of the inspection system.

5. The method of claim 1, wherein the different combinations included in the set comprise two or more of a combination of an oblique incidence illumination channel and a wide angle collection channel, a combination of the oblique incidence illumination channel and a narrow angle collection channel, a combination of a normal incidence illumination channel and the wide angle collection channel, and a combination of the normal incidence illumination channel and the narrow angle collection channel.

6. The method of claim 1, wherein the different combinations included in the set comprise two or more of a combination of an oblique incidence illumination channel and a wide angle collection channel, a combination of the oblique incidence illumination channel and a narrow angle collection channel, a combination of a normal incidence illumination channel and the wide angle collection channel, a combination of the normal incidence illumination channel and the narrow angle collection channel, and a combination of the illumination and collection channels configured for bright field differential interference contrast.

7. The method of claim 1, wherein the output acquired for the defects by at least one of the different combinations included in the set is responsive to light scattered from the defects.

8. The method of claim 1, wherein said identifying further comprises identifying the defect types of the defects based on characteristics of the output, and wherein the characteristics comprise scattering angle and intensity.

9. The method of claim 1, wherein said identifying further comprises identifying the defect types of the defects based on uniqueness of the output acquired for one of the defect types by one of the different combinations included in the set compared to the output acquired for the one of the defect types by another of the different combinations included in the set.

10. The method of claim 1, wherein said identifying further comprises identifying the defect types of the defects based on ratios of scattering signal intensity of the output acquired for the defects by the different combinations included in the set.

11. The method of claim 1, wherein said identifying further comprises determining the function of the different reported sizes for the defects separately determined from the output acquired by the different combinations included in the set and using the function as an attribute for rule based binning.

12. The method of claim 1, wherein the output acquired by the set of the different combinations comprises defect characteristics acquired by bright field differential interference contrast.

13. The method of claim 1, further comprising subtracting defects commonly detected by the different combinations included in the set from the defects detected on the wafer prior to said identifying.

14. The method of claim 1, wherein the wafer types comprise polished silicon wafers, annealed silicon wafers, epitaxial wafers, and silicon-on-insulator wafers.

15. The method of claim 1, wherein the inspection system is configured as an unpatterned wafer inspection system.

16. The method of claim 1, wherein the method is performed automatically.

17. A carrier medium, comprising program instructions executable on a computer system for performing a computer-implemented method for identifying defect types on a wafer, wherein the computer-implemented method comprises:
   acquiring output of an inspection system for defects detected on a wafer, wherein the output is acquired by different combinations of illumination and collection channels of the inspection system; and
   identifying defect types of the defects based on the output acquired by a set of the different combinations by separately determining different reported sizes for the defects from the output acquired by the different combinations included in the set and identifying the defect types of the defects based on a function of the different reported sizes for the defects, wherein the set of the different combinations is selected based on the defect types to be identified on the wafer and a wafer type of the wafer such that a different set of the different combinations of the illumination and collection channels is used for identifying different defect types on different wafer types, and wherein the defect types of the defects comprise defect types other than particles and crystal-originated pits.

18. An inspection system configured to identify defect types on a wafer, comprising:
   an optical subsystem configured to acquire output for defects on a wafer, wherein the output is acquired by different combinations of illumination and collection channels of the optical subsystem; and
   a computer system configured to identify defect types of the defects based on the output acquired by a set of the different combinations by separately determining different reported sizes for the defects from the output acquired by the different combinations included in the set and identifying the defect types of the defects based on a function of the different reported sizes for the defects, wherein the set of the different combinations is selected based on the defect types to be identified on the wafer and a wafer type of the wafer such that a different set of the different combinations of the illumination and collection channels is used for identifying different defect types on different wafer types, and wherein the defect types of the defects comprise defect types other than particles and crystal-originated pits.

* * * * *